US009539220B2

(12) United States Patent
Charney et al.

(10) Patent No.: US 9,539,220 B2
(45) Date of Patent: *Jan. 10, 2017

(54) METHODS FOR TREATING SUICIDAL IDEATION

(71) Applicants: Icahn School of Medicine at Mount Sinai, New York, NY (US); Yale University, New Haven, CT (US); The United States of America, as represented by the Secretary, Department of Health and Human Services, Rockville, MD (US)

(72) Inventors: Dennis S. Charney, New York, NY (US); Sanjay J. Mathew, New York, NY (US); Husseini K. Manji, Rockville, MD (US); Carlos A. Zarate, Rockville, MD (US); John H. Krystal, New Haven, CT (US)

(73) Assignees: Icahn School of Medicine at Mount Sinai, New York, NY (US); Yale University, New Haven, CT (US); The United States of America, as represented by The Secretary, Department of Health and Human Services, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/197,767

(22) Filed: Mar. 5, 2014

(65) Prior Publication Data

US 2014/0256821 A1   Sep. 11, 2014

Related U.S. Application Data

(63) Continuation of application No. 11/688,603, filed on Mar. 20, 2007, now Pat. No. 8,785,500.

(60) Provisional application No. 60/785,108, filed on Mar. 22, 2006.

(51) Int. Cl.
| | | |
|---|---|---|
| *A61K 31/135* | (2006.01) | |
| *A61K 31/137* | (2006.01) | |
| *A61K 9/00* | (2006.01) | |
| *A61K 9/70* | (2006.01) | |
| *A61K 45/06* | (2006.01) | |
| *A61M 15/08* | (2006.01) | |

(52) U.S. Cl.
CPC ........... *A61K 31/135* (2013.01); *A61K 9/0019* (2013.01); *A61K 9/0043* (2013.01); *A61K 9/7023* (2013.01); *A61K 31/137* (2013.01); *A61K 45/06* (2013.01); *A61M 15/08* (2013.01)

(58) Field of Classification Search
CPC .............................. A61K 31/137; A61K 31/135
USPC ....................................................... 514/647
See application file for complete search history.

(56) References Cited

U.S. PATENT DOCUMENTS

| 5,024,998 | A | * | 6/1991 | Bodor | ......................... 424/1.85 |
| 5,543,434 | A | | 8/1996 | Weg | |
| 7,973,043 | B2 | * | 7/2011 | Migaly | .................... 514/255.05 |
| 2004/0138298 | A1 | | 7/2004 | Mermelstein | |

OTHER PUBLICATIONS

Layer et al., Antidepressant-like actions of the polyamine site NMDA antagonist, eliprodil (SL-82.0715), Pharmacol. Biochem. Behav., 52:621-627,1995.
Lindefors et al., Differential effects of single and repeated ketamine administration on dopamine, serotonin and GABA transmission in rat medial prefrontal cortex, Brain Res., 759:205-212,1997.
Louon et al., Sedation with nasal ketamine and midazolam for cryotherapy in retinopathy of prematurity, Br. J. Ophthalmol., 77:529-530, 1993.
Maler et al., Memantine inhibits ethanol-induced NMDA receptor up-regulation in rat hippocampal neurons, Brain Res., 1052:156-162, 2005.
Manji et al., Enhancing neuronal plasticity and cellular resilience to develop novel, improved therapeutics for difficult-to-treat depression, Biol. Psychiatry, 53:707-742, 2003.
Marangell et al., Effects of intrathecal thyrotropin-releasing hormone (protirelin) in refractory depressed patients, Arch. Gen. Psychiatry, 54:214-222,1997.
Marlow et al., Haemodynamic response to induction of anaesthesia with ketamine/midazolam, Can. J. Anaesth., 38:844-848,1991.
McLean et al., Ketamine concentrations during cardiopulmonary bypass, Can. J. Anaesth., 43:580-584, 1996.
Meloni et al., Dizocilpine antagonizes the effect of chronic imipramine on learned helplessness in rats, Pharmacol. Biochem. Behav., 46:423-426, 1993.
Moryl et al., Potential antidepressive properties of amantadine, memantine and bifemelane. Pharmacol. Toxicol., 72:394-397,1993.
Murray et al., Global mortality, disability, and the contribution of risk factors: Global Burden of Disease Study, Lancet, 349:1436-1442,1997.
Narita et al., Role of the NMDA receptor subunit in the expression of the discriminative stimulus effect induced by ketamine, Eur. J. Pharmacol., 423:41-46, 2001.
Newcomer et al., Ketamine-induced NMDA receptor hypofunction as a model of memory impairment and psychosis, Neuropsychopharmacology, 20:106-118, 1999.
Oshima et al., Continuous subcutaneous injection of ketamine for cancer pain, Can. J. Anaesth., 37:385-386,1990.
Overall et al., The brief psychiatric rating scale, Psychol. Rep., 10:799-812, 1962.
Papp et al., Antidepressant activity of non-competitive and competitive NMDA receptor antagonists in a chronic mild stress model of depression, Eur. J. Pharmacol., 263:1-7, 1994.

(Continued)

*Primary Examiner* — Jennifer M Kim
(74) *Attorney, Agent, or Firm* — Fish & Richardson P.C.

(57) ABSTRACT

Methods and compositions for the treatment of treatment-resistant depression are described. More specifically, the invention demonstrates that intranasal administration of ketamine is effective to ameliorate the symptoms of depression in a patient who has not responded to an adequate trial of one antidepressant in the current episode and has recurrent or chronic depressive symptoms (>2 years).

9 Claims, 3 Drawing Sheets

(56) References Cited

OTHER PUBLICATIONS

Przegalinski et al., Antidepressant-like effects of a partial agonist at strychnine-insensitive glycine receptors and a competitive NMDA receptor antagonist, Neuropharmacology, 36:31-37,1997.
Rothman, Noncompetitive N-methyl-D-aspartate antagonists affect multiple ionic currents, J. Pharmacol. Exp. Ther., 246:137-142,1988.
Rush et al., Research issues in the study of difficult-to-treat depression, Biol. Psychiatry, 53:743-753,2003.
Sackeim et al., Vagus nerve stimulation (VNS) for treatment-resistant depression: efficacy, side effects, and predictors of outcome, Neuropsychopharmacology, 25:713-728, 2001.
Sackeim, The definition and meaning of treatment-resistant depression, J. Clin. Psychiatry, 62(516):10-17,2001.
Sadove et al., Analgesic effects of ketamine administered in subdissociative doses, Anesth. Analg., 50:452-457, 1971.
Sanacora et al., Subtype-specific alterations of gamma-aminobutyric acid and glutamate in patients with major depression, Arch. Gen. Psychiatry, 61 :705-713, 2004.
Sapolsky, Is impaired neurogenesis relevant to the affective symptoms of depression?, Biol. Psychiatry, 56:137-139,2004.
Skolnick et al., Adaptation of N-methyl-D-aspartate (NMDA) receptors following antidepressant treatment: implications for the pharmacotherapy of depression, Pharmacopsychiatry, 29:23-26, 1996.
Skolnick, Antidepressants for the new millennium, Eur. J. Pharmacol., 375:31-40, 1999.
Skolnick, Modulation of glutamate receptors: strategies for the development of novel antidepressants, Amino Acids, 23:153-159,2002.
Smith et al., Properties of the optical isomers and metabolites of ketamine on the high affinity transport and catabolism of monoamines, Neuropharmacology, 20:391-396, 1981.
Stannard et al., Ketamine hydrochloride in the treatment of phantom limb pain, Pain, 54:227-230, 1993.
Thase et al., Remission rates following antidepressant therapy with bupropion or selective serotonin reuptake inhibitors: a meta-analysis of original data from 7 randomized controlled trials, J. Clin. Psychiatry, 66:974-981,2005.
Thase et al., When at first you don't succeed: sequential strategies for antidepressant nonresponders, J. Clin. Psychiatry, 58(S13}:23-29, 1997.
Trivedi et al., Evaluation of outcomes with citalopram for depression using measurementbased care in STAR*D: implications for clinical practice, Am. J. Psychiatry, 163:28-40,2006.
Trullas et al., Functional antagonists at the NMDA receptor complex exhibit antidepressant actions, Eur. J. Pharmacol., 185:1-10,1990.
Vranken et al., Iontophoretic administration of S(+)-ketamine in patients with intractable central pain: a placebo-controlled trial, Pain, 118:224-231,2005.
Wang et al., NMDAINR2B selective antagonists in the treatment of ischemic brain injury, Curr. Drug Targets CNS Neurol. Disord., 4:143-151, 2005.
Wanna et al., A comparison of propofol and ketamine as induction agents for cesarean section, J. Med. Assoc. Thai., 87:774-779, 2004.
Weksler et al., Nasal ketamine for paediatric premedication, Can. J. Anaesth., 40:119-121, 1993.
White et al., Comparative pharmacology of the ketamine isomers, Br. J. Anaesth., 57:197-203,1985.
Wirz-Justice et al., Sleep deprivation in depression: what do we know, where do we go?, Biol. Psychiatry, 46:445-453, 1999.
Written Opinion of the International Searching Authority, PCT/US2007/06898, United States Patent and Trademark Office, mailed Nov. 9, 2007.
Yilmaz et al., Prolonged effect of an anesthetic dose of ketamine on behavioral despair, Pharmacol. Biochem. Behav., 71 :341-344, 2002.
Young et al., A rating scale for mania: reliability, validity and sensitivity, Br. J. Psychiatry, 133:429-435, 1978.
Zarate et al., A double-blind placebo-controlled study of memantine in major depression, Am. J. Psychiatry, 163:153-155,2006.
Zarate et al., An open-label trial of riluzole in treatment-resistant major depression, Am. J. Psychiatry, 161:171-174,2004.
Zarate et al., An open-label trial of the glutamate-modulating agent riluzole in combination with lithium for the treatment of bipolar depression, Biol. Psychiatry, 57:430-432, 2005.
Zarate et al., Modulators of the glutamatergic system: implications for the development of improved therapeutics in mood disorders, Psychopharmacol. Bulletin, 36:35-83, 2002.
Zarate et al., Regulation of cellular plasticity cascades in the pathophysiology and treatment of mood disorders: role of the glutamatergic system. Ann. NY Acad. Sci., 1003:273-291, 2003.
Andrew A. Nierenberg et al., "A Comparison of Lithium and T3 Augmentation Following Two Failed Medication Treatments for Depression: A STAR*O Report," 163(9) Am. J. Psychiatry 1519-1530 (Sep. 2006).
Mathew et al., Glutamate modulators as novel interventions for mood disorders. Revista Brasileira de Psiquiatri, 27(3): 243-8 (2005).
Sofia et al., Evaluation of ketamine HCl for anti-depressant activity. Arch. Int. de Pharacodynamie et de Therapie, 214(1): 68-74 (1975).
Zarate et al., Robust, rapid and relatively sustained antidepressant effects with a singledose of an NMDA antagonist in treatment-resistant major depression: A double-bind placebocontrolled study. Neurosychopharmacology, 30(Suppl. 1}: S245-6 (2005) (abstract 95).
Supplementary European Search Report, EP-07 75 3520, mailed Feb. 10, 2010.
Kudoh et al., Small-dose ketamine improves the postoperative state of depressed patients. Anesth. Analg. 95: 114-8 (2002).
Friedberg, HypnOSis fi<st, the dissociaNon. Anesth. Analg. 96. 913-4 (2003).
Lee et al., NMDA receptors offer more than one functionality. Anesth. Analg. 96: 1533-4.-(2003).
Ostroff et al., Antidepressant effect of ketamine during ECT. Am. J. Psychiatry. 162: 1385-6 (2005).
Correll et al., Two case studies of patients with major depressive disorder given low-dose (subanesthetic) ketamine infusions. Pain Med. 7: 92-95 (2006).
Aitken, Measurement of feelings using visual analogue scales, Proc. Royal Soc. Med., 62:989-993, 1962.
Anand et al., Attenuation of the neuropsychiatric effects of ketamine with lamotrigine: support for hyperglutamatergic effects of N-methyl-D-aspartate receptor antagonists, Arch. Gen. Psychiatry, 57:270-276, 2000.
Azevedo et al., Transderrnal ketamine as an adjuvant for postoperative analgesia after abdominal gynecological surgery using Lidocaine epidural blockade, Anesth. Anal., 91 :1479-1482, 2000.
Beck et al., Assessment of depression: the depression inventory, Modern Problems Pharmacopsychiatry, 7:151-169,1974.
Berman et al., Antidepressant effects of ketamine in depressed patients, Biol. Psychiatry, 47:351-354, 2000.
Bolshakov et al.. Determinants of trapping block of N-methyl-d-aspartate receptor channels, J. Neurochem., 87:56-65, 2003.
Bonanno et al., Ketamine in war/tropical surgery (a final tribute to the racemic mixture), Injury, 33:323-327, 2002.
Bovill et al., Alterations in response to somatic pain associated with anaesthesia, Br. J. Anaesth.,43:496-499, 1971.
Boyer et al., Chronic administration of imipramine and citalopram alters the expression of NMDA receptor subunit mRNAs in mouse brain: a quantitative in situ hybridization study, J. Mol. Neurosci.,10:219-233, 1998.
Byrd et al., Behavioral effects of phencyclidine and ketamine alone and in combination with other drugs, Eur. J. Pharmacol., 144:331-341, 1987.
Calabrese et al., A double-blind placebo-controlled study of lamotrigine monotherapy in outpatients with bipolar I depression, Lamictal 602 Study Group, J. Clin. Psychiatry, 60:79-88, 1999.
Carr et al., Safety and efficacy of intranasal ketamine for the treatment of breakthrough pain in patients with chronic pain: a randomized, double-blind, placebo-controlled, crossover study, Pain, 108:17-27, 2004.

(56) References Cited

OTHER PUBLICATIONS

Debattista et al., Acute antidepressant effects of intravenous hydrocortisone and CRH in depressed patients: a double-blind, placebo-controlled study, Am. J. Psychiatry, 157:1334-1337,2000.
Devry et al., Role of the NMDA receptor NR2B subunit in the discriminative stimulus effects of ketamine, Behav. Pharmacol., 14:229-235, 2003.
Domino et al., Pharmacologic effects of ci-581, a new dissociative anesthetic in man, Clin. Pharmacol. Ther., 40:279-291, 1965.
Drevets et al., Amphetamine-induced dopamine release in human ventral striatum correlates with euphoria, Biol. Psychiatry, 49:81-96, 2001.
D'Sa et al., Antidepressants and neuroplasticity, Bipolar Disord., 4:183-194, 2002.
Duman, Synaptic plasticity and mood disorders, Mol. Psychiatry, 7:S29-S34, 2002.
Elliott et al., N-methyl-D-aspartate (NMDA) receptors, mu and kappa opioid tolerance, and perspectives on new analgesic drug development, Neuropsychopharmacology, 13:347-356,1995.
Entsuah et al., Response and remission rates in different subpopulations with major depressive disorder administered venlafaxine, selective serotonin reuptake inhibitors, or placebo, J. Clin. Psychiatry, 62:869-877,2001.
Fava, Diagnosis and definition of treatment-resistant depression, Biol. Psychiatry, 53:649-659,2003.
Frank et al., Conceptualization and rationale for consensus definitions of terms in major depressive disorder: remission, recovery, relapse, and recurrence, Arch. Gen. Psychiatry, 48:851-855, 1991.
Gutzke et al., Cardiac transplantation: a prospective comparison of ketamine and sufentanil for anesthetic induction, J. Cardiothorac. Anesth., 3:389-95,1989.
Hamil Ton, A rating scale for depression, J. Neurol. Neurosurg. Psychiatry, 23:56-62,1960.
Hedlund et al., The Hamilton rating scale for depression, J. Operational Psychiatry, 10:149-165,1979.
Husain et al., Speed of response and remission in major depressive disorder with acute electroconvulsive therapy (ECT): a Consortium for Research in ECT (CORE) report, J. Clin. Psychiatry, 65:485-491,2004.
Hustveit et al., Interaction of the chiral forms of ketamine with opioid, phencyclidine, Hustveit et al., Interaction of the chiral forms of ketamine with opioid, phencyclidine σ and muscarinic receptors, Pharmacol. Toxicol., 77:355-359,1995.
Hyman et al., Initiation and adaptation: a paradigm for understanding psychotropic drug action, Am. J. Psychiatry, 153:151-162, 1996.
International Search Report, PCT/US2007/06898, United States Patent and Trademark Office, mailed Nov. 9, 2007.
Jick et al., Antidepressants and the risk of suicidal behaviors, JAMA, 292:338-343, 2004.
Kane et al., Clozapine and haloperidol in moderately refractory schizophrenia: a 6-month randomized and double-blind comparison, Arch. Gen. Psychiatry, 58:965-972, 2001.
Kapur et al., Ketamine has equal affinity for NMDA receptors and the high-affinity state of the dopamine 02 receptor, Biol. Psychiatry, 49:954-957, 2001.
Keller, Issues in treatment-resistant depression, J. Clin. Psychiatry, 66:5-12, 2005.
Kessler et al., Lifetime prevalence and age-of-onset distributions of DSM-IV disorders in the National Comorbidity Survey Replication, Arch. Gen. Psychiatry, 62:593-602, 2005.
Krystal et al., Comparative and interactive human psychopharmacologic effects of ketamine and amphetamine: implications for glutamatergic and dopaminergic model psychoses and cognitive function, Arch. Gen. Psychiatry, 62:985-994, 2005.
Krystal et al., Glutamate and GABA systems as targets for novel antidepressant and moodstabilizing treatments, Mol. Psychiatry, 7:S71-S80, 2002.
Krystal et al., Interactive effects of subanesthetic ketamine and haloperidol in healthy humans., PsychopharmacoloQY (Berl.), 145:193-204, 1999.
Krystal et al., Interactive effects of subanesthetic ketamine and subhypnotic lorazepam in humans, PsychopharmacoloQY (Berl.),135:213-229, 1998.
Krystal et al., Preliminary evidence of attenuation of the disruptive effects of the NMDA glutamate receptor antagonist, ketamine, on working memory by pretreatment with the group II metabotropic glutamate receptor agonist, LY354740, in healthy human subjects, Psychopharmacology (Berl.), 179:303-309, 2005.
Krystal et al., Subanesthetic effects of the noncompetitive NMDA antagonist, ketamine, in humans. Psychotomimetic, perceptual, cognitive, and neuroendocrine responses, Arch. Gen. Psychiatry, 51 :199-214,1994.
"Antidepressant Use in Children, Adolescents, and Adults", U.S. Food and Drug Administration, Protecting and Promoting Your Health, http://www.fda.gov/Drugs/DrugSafety/InformationbyDrugClass/UCM096273, dated May 2, 2007 and downloaded on Jan. 22, 2016, 2 pages.
"Leading Causes of Death", Centers for Disease Control and Prevention, CDC 24/7; Saving Lives, Protecting People, http://www.cdc.gov/nchs/fastats/leading-causes-of-death.htm, page last updated on Sep. 30, 2015 and Downloaded on Jan. 20, 2016, 2 pages.

\* cited by examiner

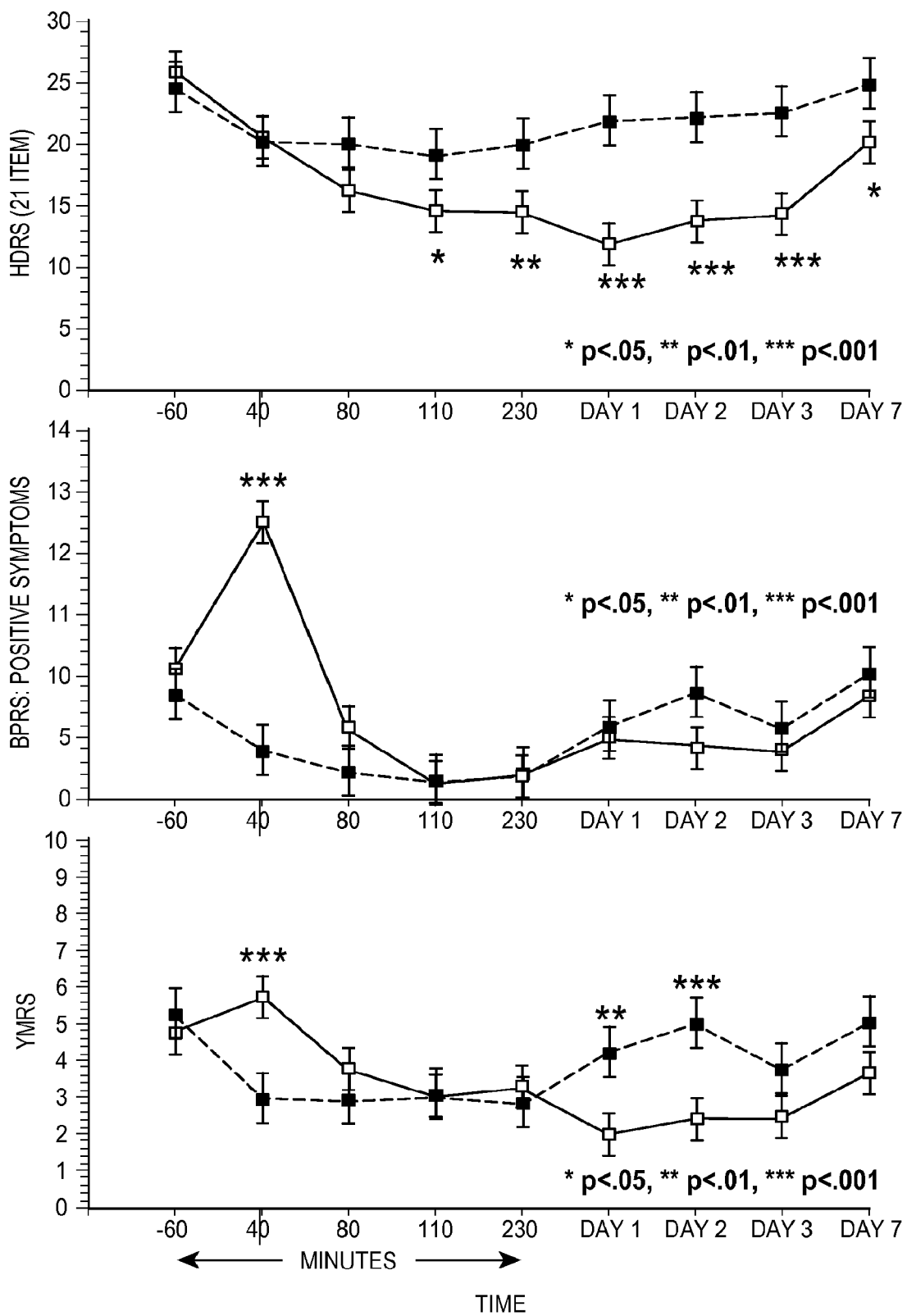

METHODS FOR TREATING SUICIDAL IDEATION

The present application is a continuation of U.S. patent application Ser. No. 11/688,603 filed Mar. 20, 2007 which claims the priority of U.S. Provisional Application No. 60/785,108 filed Mar. 22, 2006. Both of which are incorporated by reference herein in their entirety.

This invention was made with government support under Grant No. 1Z01MH002857-01 awarded by the National Institutes of Health, and a Merit Review Grant from the Department of Veterans Affairs, NIMH Program Grant. The government has certain rights in the invention.

FIELD OF THE INVENTION

The present invention relates to methods and compositions for the treatment of depression. More particularly, the invention relates to intranasal, intravenous and transdermal administration of ketamine to treat treatment-resistant depression.

BACKGROUND OF THE INVENTION

Depression is among the most disabling of all medical disorders with a lifetime prevalence of approximately 17% [1]. It frequently appears early in life, can run a chronic course, and adversely affect the prognosis of other medical illnesses, such as coronary vascular disease, diabetes, and osteoporosis.

Depression is characterized by depressed mood, and markedly diminished interest or pleasure in activities. Other symptoms include significant weight loss or weight gain, decrease or increase in appetite, insomnia or hypersomnia, psychomotor agitation or retardation, fatigue or loss of energy, feelings of worthlessness or excessive or inappropriate guilt, diminished ability to think or concentrate or indecisiveness, recurrent thoughts of death, suicidal ideation or suicidal attempts. A variety of somatic symptoms may also be present. Though depressive feelings are common, especially after experiencing setbacks in life, depressive disorder is diagnosed only when the symptoms reach a threshold and last at least two weeks. Depression can vary in severity from mild to very severe. It is most often episodic but can be recurrent or chronic. Some people have only a single episode, with a full return to premorbid function. However, more than 50 percent of those who initially suffer a single major depressive episode eventually develop another.

Depression is more common in women than in men. The point prevalence of unipolar depressive episodes is estimated to be 1.9% for men and 3.2% for women, and 5.8% of men and 9.5% of women will experience a depressive episode in a 12-month period. These prevalence figures vary across populations and may be higher in some populations. A World Health Organization study has reported that depression is the leading global cause of years of life lived with disability and the fourth leading cause of disability-adjusted life-years. Disability-adjusted life-years refers to the reduction in an individual's productive life, and is a measure that takes into account premature mortality [2].

The treatment of depression was revolutionized about a half-century ago by the serendipitous discovery of monoamine oxidase inhibitors and tricyclic antidepressants. Since then, the availability of a host of newer medications with better side effect profiles has greatly increased our ability to safely treat a significant percentage of patients. However, the newer medications are largely drugs that merely augment or otherwise potentiate the effects of the existing drugs by exerting their primary biochemical effects by increasing the intrasynaptic levels of monoamines.

Unfortunately, current medications for the treatment of depression take weeks to months to achieve their full effects and in the meantime, patients continue to suffer from their symptoms and continue to be at risk of self-harm as well as harm to their personal and professional lives. Indeed, the lag period of onset of action of several weeks of traditional antidepressants is recognized as a major limitation, resulting in considerable morbidity and high risk of suicidal behavior especially in the first 9 days of starting antidepressants [3]. Pharmacological strategies that have rapid onset of antidepressant effects within hours or a few days and that are sustained would therefore have an enormous impact on public health.

Recently, an "initiation and adaptation" paradigm for understanding the delayed therapeutic actions of antidepressants has been proposed [4]. This paradigm posits that the effect of acute drug administration is mediated via an initial direct target protein perturbation (e.g. binding to a monoamine transporter, thereby resulting in monoamine reuptake inhibition); with repeated administration, the same initial event, over time, leads to enduring adaptive changes in critical neuronal networks, thereby resulting in stable long-term antidepressant effects. Thus, this paradigm posits that the delay in the therapeutic actions of existing pharmacologic agents is due to the fact that they initially act on proteins, which are considerably upstream of the target genes, which are ultimately responsible for the antidepressant effects. In this context, the major systems that have been postulated to mediate the delayed adaptive effects of antidepressants are neurotrophic signaling cascades and the glutamatergic system [5].

The actions of antidepressants on neurotrophic signaling cascades has been discussed by a number of groups [6-8]. The context of the present application is with respect to the role of the glutamatergic system, most notably the NMDA system, in the actions of antidepressants [9-11], reviewed in [12]. NMDA receptor antagonists have antidepressant effects in many animal models of depression, including the application of inescapable stressors, forced-swim, and tail suspension-induced immobility tests, in learned helplessness models of depression, and in animals exposed to a chronic mild stress procedure [13-18]. A single dose of the NMDA antagonist ketamine in male Wistar rats interferes with the induction of behavioral despair for up to 10 days after its administration [19]. Additionally, repeated administration of different classes of antidepressants—in a time frame consistent with the delayed therapeutic effects—brings about alterations in the expression of NMDA subunit mRNA [20] and radioligand binding to these receptors in regions of the brain implicated in the pathophysiology of depression [9].

Several lines of evidence also suggests that dysfunction of the glutamatergic system may play an important role in the pathophysiology of depression [reviewed in 21, 22]. Notably, a recent study by Sanacora et al. showed glutamate levels in the occipital cortex to be significantly elevated, in 29 medication-free subjects with unipolar major depression, as compared to 28 age- and gender-matched healthy controls [23]. Together, these data support the hypothesis of regional alterations in glutamatergic signaling in mood disorders. Finally, in clinical trials, the glutamatergic modulators lamotrigine and riluzole (both inhibitors of glutamate release) were found to have antidepressant properties [24-26].

Ketamine has been used in the treatment of breakthrough pain (BTP) in chronic pain patients. In such patients, 10-50 mg of ketamine has been administered through intranasal administration in incremental 10 mg doses, every 90 seconds. The effect of that intranasal administration of ketamine was that there was a lower BTP in patients that received intranasal ketamine as opposed to placebo. There were very few side effects with such administration [47].

Transdermal administration of ketamine has also been used for the treatment of intractable neuropathic pain [87]. Results indicated that subjects given a dose of 75 mg showed significant improvement in pain disability, and subjective physical and mental function. Azevedo et al. [88] report the results of a randomized, double-blind, placebo-controlled trial using racemic ketamine in a transdermal delivery system after minor abdominal gynecological surgery using lidocaine epidural blockade. At the end of the surgical procedure, a controlled delivery transdermal patch containing either ketamine (25 mg/24 hours) or placebo was applied. The time to rescue analgesic was longer in the ketamine group (230±112 minutes) compared to the placebo group (94±54 minutes).

The limitations in sustaining disorder remission are increasingly apparent for standard treatments of treatment-resistant depression. The first phase of the STAR*D study, the largest effectiveness study of its kind in "real world" patients, measured the efficacy of a SSRI, citalopram, in outpatients with depression (n=2,876). Remission rates were 28%, a similar remission rate to that achieved in standard randomized placebo-controlled acute efficacy trials [48]. As the presence of residual symptoms is a strong predictor of relapse or recurrence [49], therapeutic strategies going forward require a focus on achieving and sustaining remission, by presumably addressing core pathophysiological processes. Thus, it is evident that new methods are needed for the treatment of chronic major depression that is resistant to treatment.

SUMMARY OF THE INVENTION

Methods and compositions for the treatment of treatment-resistant depression are described. More specifically, the invention demonstrates that intranasal administration of ketamine is effective to ameliorate the symptoms of treatment-resistant depression. In particular embodiments, the invention thus provides a method of treating a human patient for treatment-resistant depression, comprising intranasally administering a composition comprising ketamine to the patient at a dosage sufficient to reduce or eliminate the symptoms of the treatment-resistant depression. In more specific embodiments, the ketamine is in a pharmaceutically acceptable carrier and is administered at a dose of between about 0.1 mg/kg per day to about 3.0 mg/kg/day.

In specific embodiments, the symptoms of the treatment-resistant depression are alleviated within 2 hours of intranasal administration of the ketamine.

The methods of the invention may be achieved through a method that comprises intranasal administration of a single dose of the ketamine. Alternatively, multiple doses of ketamine may be administered. In specific embodiments, a single intranasal administration of the ketamine is sufficient to alleviate the effects of the depression for 7 days, and in some cases, longer.

In other aspects of the invention, the method may further comprise administering a pharmaceutically effective dose of a second agent, wherein the second agent is an antidepressant agent. The additional agent may be any addition antidepressant agent. Exemplary such antidepressant agents include but are not limited to at least one member of lithium, a pharmaceutical antidepressant, an herbal antidepressant, an anticonvulsant, a mood stabilizer, an antipsychotic agent, and a benzodiazepine.

Also contemplated herein is a kit comprising a carrier for delivering a ketamine intranasally containing in close confinement therein one or more components, wherein: a) a first component contains ketamine; and b) a second component contains a psychotropic medication useful in the treatment of depression. In a further aspect of the invention, the second component is selected from the group consisting of lithium, pharmaceutical antidepressant, an herbal antidepressant, an anticonvulsant, a mood stabilizer, an antipsychotic agent, and a benzodiazepine.

Also provided in the present invention is a device for patient self-administration of ketamine comprising a nasal spray inhaler containing an aerosol spray formulation of ketamine and a pharmaceutically acceptable dispersant, wherein the device is metered to disperse an amount of the aerosol formulation by forming a spray that contains a dose of ketamine effective to alleviate depression but which dose of ketamine is determined by a physician or medical care provider to be below a level that causes dysphoria or psychosis.

In alternative embodiments, intravenous and transdermal administration of ketamine are contemplated. In one alternative embodiment, the invention thus provides a method of treating a human patient for treatment-resistant depression, comprising intravenously administering a composition comprising ketamine to the patient at a dosage sufficient to reduce or eliminate the symptoms of the treatment-resistant depression. In another alternative embodiment, the invention thus provides a method of treating a human patient for treatment-resistant depression, comprising transdermally administering a composition comprising ketamine to the patient at a dosage sufficient to reduce or eliminate the symptoms of the treatment-resistant depression. In more specific embodiments, the ketamine is in a pharmaceutically acceptable carrier and is administered at a dose of between about 0.1 mg/kg per day to about 3.0 mg/kg/day.

In specific embodiments, the symptoms of the treatment-resistant depression are alleviated within 2 hours of administration of the ketamine.

The methods of the invention may be achieved through a method that comprises intravenous or transdermal administration of multiple doses of the ketamine. In specific embodiments, the ketamine is administered at least two, at least three, at least four, at least five, at least six, at least seven, at least eight, at least nine times in fourteen days. In other embodiments, the ketamine is administered at least two, at least three, at least four, at least five, at least six, at least seven, at least eight, at least nine times in twenty-one days.

In other aspects of the invention, the method may further comprise administering a pharmaceutically effective dose of a second agent, wherein the second agent is an antidepressant agent. The additional agent may be any addition antidepressant agent. Exemplary such antidepressant agents include but are not limited to at least one member of lithium, a pharmaceutical antidepressant, an herbal antidepressant, an anticonvulsant, a mood stabilizer, an antipsychotic agent, and a benzodiazepine.

Also provided in the present invention is a device for patient self-administration of ketamine comprising a transdermal patch containing a formulation of ketamine and a pharmaceutically acceptable carrier, wherein the device is metered to disperse an amount of the formulation that contains a dose of ketamine effective to alleviate depression but which dose of ketamine is determined by a physician or medical care provider to be below a level that causes dysphoria.

Other features and advantages of the invention will become apparent from the following detailed description. It should be understood, however, that the detailed description and the specific examples, while indicating preferred embodiments of the invention, are given by way of illustration only, because various changes and modifications within the spirit and scope of the invention will become apparent to those skilled in the art from this detailed description.

BRIEF DESCRIPTION OF THE DRAWINGS

The following drawings form part of the present specification and are included to further illustrate aspects of the present invention. The invention may be better understood by reference to the drawings in combination with the detailed description of the specific embodiments presented herein.

FIG. 2 Change in 21 HDRS, BPRS positive symptoms and YMRS scores over one week (n=18). Abbreviations: BPRS Brief Psychiatric Rating Scale; HDRS: Hamilton Depression Rating Scale; YMRS: Young Mania Rating Scale.

DETAILED DESCRIPTION OF THE PREFERRED EMBODIMENTS OF THE INVENTION

Figure 1:
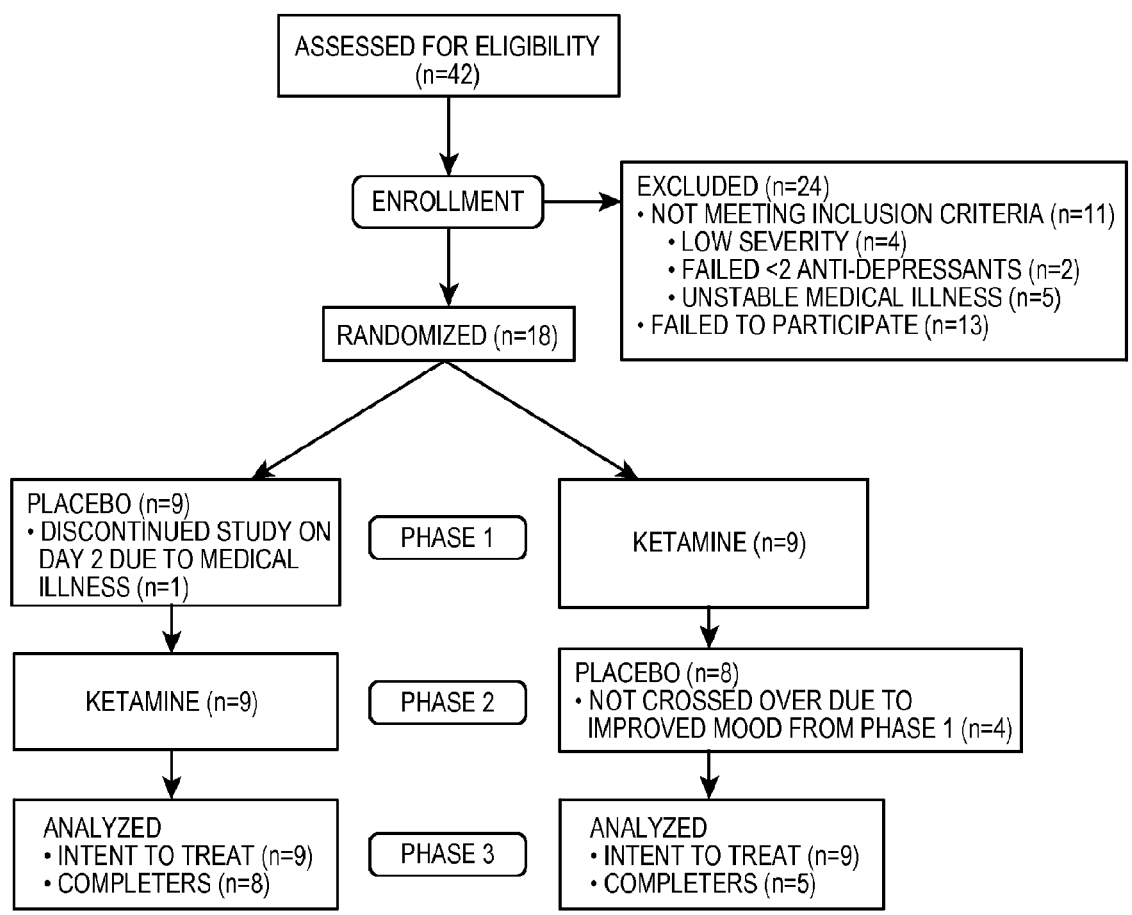
FIG. 1 Enrollment, randomization, withdrawals and completion of the two treatment phases (n=18)

Existing therapies for major depression have a lag of onset of action of several weeks, resulting in considerable morbidity and high risk of suicidal behavior. Exploring pharmacological strategies that have rapid onset of antidepressant effects within a few days and that are sustained would have an enormous impact on patient care. Converging lines of evidence suggest the role of the glutamatergic system in the pathophysiology and treatment of mood disorders.

Based on the preclinical and preliminary clinical studies, the inventors postulated that the NMDA receptor complex may mediate the delayed therapeutic effects of traditional monoaminergic based antidepressants, and furthermore that directly targeting the NMDA receptor would bring about rapid antidepressant effects. Indeed, in a preliminary study of 7 subjects with major depression, it was reported that a single intravenous dose of the high-affinity NMDA receptor antagonist ketamine resulted in a rapid and short-lived antidepressant effect [27]. In the present invention, the inventors have performed studies to determine if ketamine does indeed exert rapid antidepressant effects in a relatively refractory population, and furthermore, if these effects of a single dose of ketamine are sustained.

The exemplary data provided herein were obtained from a randomized, placebo-controlled, double-blind crossover study on patients that had DSM-TV (Diagnostic and Statistical Manual of Mental Disorders, fourth edition; DSM-IV) treatment-resistant major depression. The term "treatment-resistant major depression" refers to the depression experienced by any subject who has not previously responded to two adequate antidepressant trials (adequacy of antidepressant trials were determined with the Antidepressant Treatment History Form). Treatment-resistant major depression is a relatively common occurrence in clinical practice, with up to 50 to 60% of patients not achieving adequate response following antidepressant treatment [52]. At a minimum, treatment resistant-depression includes unipolar depression that does not respond satisfactorily to one or more treatments that are optimally delivered [53]. If the depression has not benefited from at least two adequate trials of medications from different classes in the current episode, clinically significant resistance is present [54]. Several schemes to "stage" the degree of resistance have been proposed. The most widely accepted scheme uses the staging system of Thase and Rush [55]. The stages of resistance are as follows:

Stage I: Failure of at least one adequate trial of one major class of antidepressant;

Stage II: Stage I resistance plus failure of adequate trial of an antidepressant in a distinctly different class from that used in Stage I Stage III: Stage II resistance plus failure of an adequate trial of a TCA Stage IV: Stage III resistance plus failure of an adequate trial of a MAOI Stage V: Stage IV resistance plus failure of a course of bilateral ECT Thus, from the above schemes, the skilled person may understand treatment-resistant depression patients to include patients that have failed to respond to one adequate trial of an antidepressant (Stage I).

Another staging system takes into consideration both the number of failed trials as well as the intensity/optimization of each trial, and does not make assumptions regarding a hierarchy of antidepressant classes. Massachusetts General Hospital (MGH) Staging Method to Classify Treatment-Resistant Depression:

(1) Non-response to each adequate (at least 6 weeks of an adequate dose of antidepressant) trial of a marketed antidepressant generates an overall score of resistance (1 point per trial);

(2) Optimization of dose, optimization of duration, and augmentation/combination of each trial (based on the MGH or Antidepressant Treatment Response Questionnaire) increase the overall score (0.5 point per trial per optimization/strategy);

(3) ECT increases the overall score by 3 points ECT, electroconvulsive therapy.

Finally, many researchers use the guidelines proposed by the Antidepressant Treatment History Form (ATHF, Sackeim 2001, Neuropsychopharmacology 25: 713-728). The Antidepressant Treatment History Form defines the adequacy of the treatment on a continuum for both dose and duration, providing categories rated 0 through 4. The ATHF provides for different levels of resistance. A level 3 degree of resistance for fluoxetine, for example, requires at least 4 weeks of fluoxetine at at least 20 mg/day. Although they are somewhat arbitrary, these benchmarks do reflect reasonable clinical distinctions among previous treatment trials. Validation of this approach has been achieved for acute phase treatment response to electroconvulsive therapy (ECT) and vagus nerve stimulation (VNS).

Thus, the patient population to be treated by the present invention may be defined according to any one or more of the above schemes. After a 2-week drug-free period, exemplary subjects having treatment-resistant depression were given an intravenous infusion of either ketamine hydrochloride (0.5 mg/kg) or placebo on 2 test days, a week apart. Subjects were rated at baseline and at 40, 80 minutes, 110 minutes, 230 minutes and days 1, 2, 3 and 7 post-infusion. The outcome of the treatment was measured using changes in scores on the primary efficacy to measure the 21-item Hamilton Depression Rating Scale (HDRS). From these studies it was shown that subjects on ketamine showed significant improvement in depression compared to placebo within 110 minutes after injection that remained significant throughout the following week. The effect size for the drug difference was very large (d=1.46, 95% C.I. 0.91-2.01) after 24 hours and moderate to large (d=0.68, 95% C.I. 0.13-1.23)) after 1 week. Of the subjects treated with ketamine, 71% met response and 29% met remission criteria the day following ketamine infusion. Thirty-five percent of subjects maintained response for at least 1 week. From these data it can be concluded that robust and rapid antidepressant effects can result from a single intravenous dose of an NMDA antagonist; onset of improvement was evident within 2 hours post-infusion and continued to remain significant for 1 week.

The present invention is directed to methods and compositions for treating treatment-resistant depression using intranasal administration of ketamine. Such a treatment may be administered alone or may be supplemented with other antidepressant therapies as described below.

Intravenous administration of ketamine also has been used for the treatment of treatment-resistant major depression. In that study, a 0.5 mg/kg intravenous infusion was given over 40 minutes. Improvements in depression were seen within 2 hours post-injection; and continued for up to 1 week. There were no serious adverse events; ceased within 80 min post-infusion (euphoria, elevated BP, increased libido, perceptual disturbances; Zarate et al, 2006).

Intranasal (IN) ketamine plasma levels used for pain is 3-4 fold lower than the intravenous (IV) ketamine studies in depression [27, 78-86]. The slow infusion of ketamine produces gradually increasing plasma levels during the infusion period. Dose-wise, the typical ketamine dose for surgical induction is between 1.0-2.0 mg/kg, with additional ketamine used to sustain anesthesia. In anesthesia, the target ketamine blood level is reached with ketamine bolus doses between 0.2-0.26 mg/kg over 1 min, so the dose for anesthesia is around 5 times less than the IV dose. The dose for ketamine plasma levels to produce antidepressant responses as opposed to the levels needed to produce anesthesia is in the range of 0.5 mg/kg over 40 min. The reports of dissociation in the Can study and other pain studies were significantly lower than the IV studies in MDD because the ketamine levels achieved intranasally in these studies were much lower. The intranasal dose used for pain (50 mg) is roughly equivalent to 0.1 mg/kg i.v. of ketamine.

In the present invention, the methods described are for the treatment of depression in which up to 50 mg of ketamine is administered intranasally. Such an administration may be administered over a 1 hour time period or more or less. As depression is a chronic illness requiring maintenance treatment, it is expected that chronic administration of the intranasal formulation may be employed as necessary, ranging from daily to weekly, depending on response. Should the 50 mg IN dosage prove to be inadequate to treat depression effectively increasing doses, e.g., approximately 100 mg, approximately 150 mg, approximately 200 mg, approximately 250 mg total ketamine will be administered intranasally, to establish the relative equivalent of the 0.5 mg/kg dosage usage in the TV studies.

The intranasal administration of ketamine will be well tolerated at the dosage used. In terms of efficacy, it is contemplated that the positive results seen with treatment of depression using an IV route of administration will be observed with the intranasal.

In some embodiments, the intranasal ketamine formulation will be used for an outpatient group of depressed patients who are considered treatment-resistant. The intranasal formulation will eliminate the necessity of patient presentation to a hospital or clinic for intravenous administration. The patient can take intranasal ketamine in their own home, with no need for a needle stick. Thus, the acceptability of the treatment for patients will be better than with the TV ketamine. The patient may be one that is at least a moderately treatment-resistant patient, who is seeking new options for the rapid and safe reduction of depressive symptoms. The physician would monitor the patient as an outpatient, and could adjust dosage as they would for an orally administered medication.

Ketamine ((2-(2-chlorophenyl)-2-(methylamino)-cyclohexanone) is a general anesthetic used by anesthesiologists, veterinarians, and researchers. Nasal administration of ketamine and midazolam to achieve sedation for ophthalmic surgery, and to induce anesthesia prior to elective surgery in healthy children has been reported [50, 51]. Usually, ketamine is administered intramuscularly (i.m.) or intravenously (i.v.) to induce anesthesia. However, intranasal compositions of ketamine are available from e.g., Javelin Pharmaceuticals.

Ketamine has also been known to have analgesic properties [56]; analgesia can be achieved with subanesthetic doses of ketamine [57, 58]. The drug is administered by various routes, including i.v., i.m., caudal, intrathecal, and subcutaneous (s.c.). Subcutaneous administration of ketamine has been used to treat pain following surgery and associated with terminal cancer [see, e.g., 59]. Ketamine hydrochloride administered via a subcutaneous cannula was reported to successfully treat phantom limb pain [60].

As explained above, management of treatment-resistant depression is complex and frequently unsuccessful. In the present invention, it is shown that non-competitive N-methyl-D-aspartate (NMDA) receptor antagonists, such as ketamine, will form a first line defense against treatment-resistant depression if administered through the nasal route.

The present invention is broadly directed to a method for treating treatment-resistant depression. More particularly, the inventors have discovered that administration via a nasal route of a dose of ketamine is effective to alleviate depression in patients suffering from treatment resistant depression. In a further embodiment, the present invention provides for pulmonary administration of ketamine by inhalation. Nasal administration of an anti-depressant dose of ketamine advantageously allows for patient self administration of the drug, which provides for depression management on an outpatient basis. Moreover, ketamine administration in nasal sprays and inhalers are generally socially acceptable.

Another advantage of the invention is that it allows the administration of lesser amount of a second anti-depressant agent for the treatment of treatment-resistant depression. As such, in some embodiments, the intranasal administration of the ketamine may have an additive effect when administered in combination with another antidepressant.

Ketamine is an inexpensive, readily available drug, with minor adverse side effects. Thus, the invention contemplates additional savings to the overburdened health care system.

Nasal administration of this agent is rapid, allowing for fast action of the drug, and easily accomplished by a non-medically trained patient.

In one aspect, the depression-alleviating dose of ketamine is approximately 0.01 to approximately 1 mg/kg of body weight. In a more preferred aspect, the dose of ketamine is approximately 0.05 to approximately 0.7 mg/kg of body weight. In another embodiment, the total dose of ketamine per nasal administration ranges from about 1 to about 250 mg.

In a specific aspect of the invention, the dose of ketamine is effective to alleviate depression in a patient suffering from treatment-resistant depression. In a particular aspect, nasal administration of ketamine can be a supplemental therapy in a depression management regimen that include administration of one or more additional antidepressant agents. Such additional agents may be administered through a nasal route or through another route. The additional agents may be administered concurrently with the ketamine or before or after the ketamine administration.

The ketamine may be provided in a metered dose which is well below the level associated with dysphoria or hallucination. In other aspects the dose of the second antidepressant agent is provided in an amount effective to alleviate depression with the ketamine; preferably the second antidepressant agent is administered via the mucosal route with the ketamine.

The invention provides a device for patient self-administration of ketamine, which device comprises a nasal inhaler containing an aerosol formulation of ketamine and a pharmaceutically acceptable dispersant, wherein the device is metered to disperse an amount of the aerosol formulation that contains a dose of ketamine effective to alleviate depression. The dispersant may be a surfactant, such as, but not limited to, polyoxyethylene fatty acid esters, polyoxyethylene fatty acid alcohols, and polyeoxyethylene sorbitan fatty acid esters. Phospholipid-based surfactants also may be used.

In other embodiments, the aerosol formulation of ketamine is provided as a dry powder aerosol formulation in which the ketamine is present as a finely divided powder. The dry powder formulation can further comprise a bulking agent, such as, but not limited to, lactose, sorbitol, sucrose and mannitol.

In another specific embodiment, the aerosol formulation is a liquid aerosol formulation further comprising a pharmaceutically acceptable diluent, such as, but not limited to, sterile water, saline, buffered saline and dextrose solution.

In further embodiments, the aerosol formulation further comprises a second antidepressant agent in a concentration such that the metered amount of the aerosol formulation dispersed by the device contains a dose of the second agent in a metered amount that is effective to ameliorate the symptoms of depression when used in combination with the ketamine.

Thus, the invention provides a self administration method for outpatient treatment of treatment-resistant depression. Such administration may be used in a hospital, in a medical office or outside a hospital or medical office by non-medical personnel for nasal self administration of ketamine.

The present invention is based on the surprising and unexpected discovery that nasal administration of ketamine can alleviate symptoms of chronic, treatment-resistant depression. Thus, patients that have previously been refractory to treatment with antidepressants, was able to achieve more satisfactory depression management by nasal administration of 8-32 mg of ketamine, corresponding to [0.13 to 0.53] mg/kg of body weight. However, it is contemplated that up to 250 mg of ketamine may be administered intranasally for the treatment of depression. In one preferred embodiment, a ketamine dosage of 0.5 mg/kg was effective to improve mood at 40 minutes through 7 days in patients that previously manifested treatment-resistant depression. The invention shows a robust and rapid (within hours of intranasal administration) and relatively sustained (effects lasting 1 week) response to even a single-dose of the NDMA antagonist ketamine. Notably, subjects treated with intranasal ketamine were better than placebo within 2 hours (110 minutes) and remained better through 7 days. In addition, the invention also shows that IV administration of f ketamine can alleviate symptoms of chronic, treatment-resistant depression. Thus, patients that have previously been refractory to treatment with antidepressants, was able to achieve more satisfactory depression management by IV administration of ketamine. Again, subjects treated with IV ketamine were better than placebo within 2 hours (110 minutes) and remained better through 7 days.

Any chronic, treatment-resistant depression may be treated by the methods described herein. Such depression may include but is not limited to any of: major depressive disorder, single episode, recurrent major depressive disorder-unipolar depression, seasonal affective disorder-winter depression, bipolar mood disorder-bipolar depression, mood disorder due to a general medical condition-with major depressive-like episode, or mood disorder due to a general medical condition-with depressive features, wherein those disorders are resistant to treatment in a given patient. Thus, any patient that presents one of those disorders and who has not responded to an adequate trial of one antidepressant in the current episode and has recurrent or chronic depressive symptoms for greater than 2 years can be treated by the methods of the invention. Manic Depressive illnesses are also described in Goodwin, et al., [61].

There are three types of depression generally characterized in the art, major depression, dysthymic disorder, or dysthymia, and depressive disorder not otherwise specified. Major depression is characterized by peak episodes of extreme depression. During a peak episode, the patient may suffer from depressed mood, and markedly diminished interest or pleasure in activities. Other symptoms include significant weight loss or weight gain, decrease or increase in appetite, insomnia or hypersomnia, psychomotor agitation or retardation, fatigue or loss of energy, feelings of worthlessness or excessive or inappropriate guilt, diminished ability to think or concentrate or indecisiveness, recurrent thoughts of death, suicidal ideation or suicidal attempts. Symptoms last for at least two weeks and cause significant distressor impairment in important areas of functioning.

Dysthymia is characterized by depressed mood for at least 2 years as well as other symptoms like poor appetite or overeating, insomnia or hypersomnia, low energy or fatigue, low self esteem, poor concentration or difficulty making decisions and feelings of hopelessness. As is recognized in the field of psychiatric arts, depression may also comprise, and/or may also manifest itself in a variety of forms, including but not limited to, seasonal affective disorder, diurnal mood variations, or depression associated with menopause. Diagnostic criteria for dysthymia and major depression, as well as for seasonal affective disorder, diurnal mood variations and depression associated with menopause, are more fully explained in the Diagnostic and Statistical Manual of Mental Disorders, Fourth Edition, (DSM IV) published by the American Psychiatric Association or by the ICD (ICD-10: International Statistical Classification of Diseases and Related Health Problems (10th Revision) or any other psychiatric classification system.

Depression with seasonal affective pattern or seasonal affective disorder (hereinafter referred to as "SAD") is also known as cabin fever, evening blues, and sun deprivation syndrome. The terms "seasonal affective disorder" or "seasonal pattern specifier" are defined in the DSM-IV as a specifier or adjective that more precisely characterize feature associated with depression. A particular feature of SAD is the regular occurrence of depression in winter.

Most of the patients with SAD are characterized by an atypical type of depression in the winter which is associated with mood reactivity (mood brightens in response to actual or potential positive events) as well as weight gain or increase in appetite, hypersomnia, leaden paralysis (heavy, leaden feelings in arms or legs), long-standing pattern of interpersonal rejection sensitivity.

The diagnosis of depression usually follows a clinical evaluation by a psychiatrist or other mental health professionals. The two most recognized sets of diagnostic criteria for major depressive disorder and other depressive, or mood disorders, are outlined in the DSM, Diagnostic and Statistical Manual of Mental Disorders, Fourth Edition, (DSM IV) published by the American Psychiatric Association and the ICD (ICD-10: International Statistical Classification of Diseases and Related Health Problems-10th Revision, published periodically by the World Health Organization) or any other psychiatric classification system.

The presence and the severity of the depressive state can also be determined with structured and semi-structured interview and questioners such as the Hamilton score that is well known in the art. [62]. Accordingly, the present invention is directed of methods for alleviating treatment-resistant depression on an outpatient basis by nasal administration of ketamine, and to devices usable by non-medical personnel for nasal self-administration of ketamine.

Ketamine will preferably be prepared in a formulation or pharmaceutical composition appropriate for nasal administration. Suitable formulations are discussed in detail, infra. In a further embodiment, ketamine can be formulated with a mucosal penetration enhancer to facilitate delivery of the drug. The formulation can also be prepared with pH optimized for solubility, drug stability, absorption through nasal mucosa, and other considerations.

The invention provides for administration of a therapeutically effective dose of ketamine, i.e., a dose effective to alleviate treatment-resistant depression. The actual dose will vary, depending on the body weight of the patient, the severity of the depression, the route of administration, the nature of medications administered concurrently, the number of doses to be administered per day, and other factors generally considered by the ordinary skilled physician in the administration of drugs. In a specific embodiment, the amount of ketamine administered to a patient suffering from treatment-resistant depression is about 10% to about 20% of the amount used to induce anesthesia. In another specific embodiment, the dose of ketamine is about 0.01 mg per kg of body weight (0.01 mg/kg) to about 1 mg/kg; preferably about 0.05 mg/kg to about 0.7 mg/kg. In yet another embodiment, the dose ranges from about 1 mg to about 250 mg. A dose of any integer between these two numbers is contemplated. Thus, for example, intranasal, transdermal, intravenous, intradermal, or subcutaneous formulations respectively containing total intranasal, transdermal, intravenous, intradermal, or subcutaneous doses of 1 mg, 2 mg, 4 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg are specifically contemplated. Preferably, the effective dose is titrated under the supervision of a physician or medical care provider, so that the optimum dose for the particular application is accurately determined. Thus, the present invention provides a dose suited to each individual patient.

Once the dosage range is established, a further advantage of the invention is that the patient can administer ketamine on an as-needed, dose-to-effect basis. Thus, the frequency of administration is under control of the patient. However, the relatively low dose with each administration will reduce the possibilities for abuse.

Yet another particular advantage of the present invention is that nasal administration of ketamine is non-invasive, and provides for introduction into the bloodstream almost as fast as i.v. administration, and much faster than perioral administration.

More importantly, a patient can control administration of the antidepressant medication, because nasal administration provides for precise control over the dosage and effect of the drug used to offset changes in depression throughout an administration period. Nasal administration of ketamine optimally provides for dose-to-effect administration of the drug.

The term "nasal administration" in all its grammatical forms refers to administration of a drug through the nasal mucous membrane to the bloodstream for systemic delivery of the drug. The advantages of nasal administration for drug delivery are that it does not require injection using a syringe and needle, it avoids necrosis that can accompany i.m. administration of drugs, and trans-mucosal administration of a drug is highly amenable to self administration.

The present invention contemplates pulmonary administration through an inhaler.

The ketamine may be formulated with a "mucosal penetration enhancer," i.e., a reagent that increases the rate or facility of transmucosal penetration of ketamine, such as but not limited to, a bile salt, fatty acid, surfactant or alcohol. In specific embodiments, the permeation enhancer can be sodium cholate, sodium dodecyl sulphate, sodium deoxycholate, taurodeoxycholate, sodium glycocholate, dimethylsulfoxide or ethanol.

A "therapeutically effective amount" of a drug is an amount effective to demonstrate a desired activity of the drug. According to the instant invention, a therapeutically effective amount of ketamine is an amount effective to alleviate, i.e., noticeably reduce, the symptoms of treatment-resistant depression patient.

Those skilled in the art are well aware of nasal administration of ketamine for treating pain (see U.S. Pat. No. 5,543,4354, incorporated herein by reference in its entirety) Through such nasal and pulmonary administration of ketamine and additional therapeutically active drugs or agents with which ketamine can be administered to treat depression as discussed herein.

The present invention contemplates formulations comprising ketamine for use in a wide variety of devices that are designed for the delivery of pharmaceutical compositions and therapeutic formulations to the respiratory tract, preferably the nasal passages. The preferred route of administration of the present invention is in an aerosol spray for nasal inhalation. Ketamine, combined with a dispersing agent, or dispersant, can be administered in an aerosol formulation as a dry powder or in a solution or suspension with a diluent.

As used herein, the term "aerosol" refers to suspension in the air. In particular, aerosol refers to the particlization or atomization of a formulation of the invention and its suspension in the air. According to the present invention, an aerosol formulation is a formulation comprising ketamine for nasal inhalation or pulmonary administration.

As used herein, the term "inhaler" refers both to devices for nasal and pulmonary administration of a drug, e.g., in solution, powder and the like. For example, a the term "inhaler" is intended to encompass a propellant driven inhaler, such as is used for to administer antihistamine for acute asthma attacks, and plastic spray bottles, such as are used to administer decongestants.

As used herein, the term "dispersant" refers to an agent that assists aerosolization of the ketamine or absorption of the ketamine in mucosal tissue, or both. In a specific aspect, the dispersant can be a mucosal penetration enhancer. Preferably, the dispersant is pharmaceutically acceptable. As used herein, the term "pharmaceutically acceptable" means approved by a regulatory agency of the Federal or a state government or listed in the U.S. Pharmacopeia or other generally recognized pharmacopeia for use in animals, and more particularly in humans.

Suitable dispersing agents are well known in the art, and include but are not limited to surfactants and the like. Such surfactants are generally used in the art to reduce surface induce aggregation of ketamine caused by atomization of the solution forming the liquid aerosol and may be used in the methods and devices of the present invention. Examples of such surfactants include, but are not limited to, surfactants such as polyoxyethylene fatty acid esters and alcohols, and polyoxyethylene sorbitan fatty acid esters. Amounts of surfactants used will vary, being generally within the range or 0.001 and 4% by weight of the formulation. Suitable surfactants are well known in the art, and can be selected on the basis of desired properties, depending on the specific formulation, concentration of ketamine, diluent (in a liquid formulation) or form of powder (in a dry powder formulation), etc.

The liquid aerosol formulations contain ketamine and a dispersing agent in a physiologically acceptable diluent. The dry powder aerosol formulations of the present invention consist of a finely divided solid form of ketamine and a dispersing agent. With either the liquid or dry powder aerosol formulation, the formulation must be aerosolized. That is, it must be broken down into liquid or solid particles in order to ensure that the aerosolized dose actually reaches the mucous membranes of the nasal passages or the lung. The term "aerosol particle" is used herein to describe the liquid or solid particle suitable for nasal or pulmonary administration, i.e., that will reach the mucous membranes. Other considerations, such as construction of the delivery device, additional components in the formulation, and particle characteristics are important. These aspects of nasal or pulmonary administration of a drug are well known in the art, and manipulation of formulations, aerosolization means and construction of a delivery device require at most routine experimentation by one of ordinary skill in the art.

In a particular embodiment, the mass median dynamic diameter will be 5 micrometers or less in order to ensure that the drug particles reach the lung alveoli (Wearley, L. L., 1991, 1991, Crit. Rev. in Ther. Drug Carrier Systems 8:333).

With regard to construction of the delivery device, any form of aerosolization known in the art, including but not limited to spray bottles, nebulization, atomization or pump aerosolization of a liquid formulation, and aerosolization of a dry powder formulation, can be used in the practice of the invention.

As noted above, in a preferred aspect of the invention, the device for aerosolization is a metered dose inhaler. A metered dose inhaler provides a specific dosage when administered, rather than a variable dose depending on administration. Such a metered dose inhaler can be used with either a liquid or a dry powder aerosol formulation. Metered dose inhalers are well known in the art.

For nasal administration, a useful device is a small, hard bottle to which a metered dose sprayer is attached. In one embodiment, the metered dose is delivered by drawing the ketamine solution into a chamber of defined volume, which chamber has an aperture dimensioned to aerosolize and aerosol formulation by forming a spray when a liquid in the chamber is compressed. The chamber is compressed to administer the ketamine. In a specific embodiment, the chamber is a piston arrangement. Such devices are commercially available.

Alternatively, a plastic squeeze bottle with an aperture or opening dimensioned to aerosolize an aerosol formulation by forming a spray when squeezed. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the drug.

Often, the aerosolization of a liquid or a dry powder formulation for inhalation into the lung will require a propellent. The propellent may be any propellant generally used in the art. Specific nonlimiting examples of such useful propellants are a chloroflourocarbon, a hydrofluorocarbon, a hydochlorofluorocarbon, or a hydrocarbon, including trifluoromethane, dichlorodiflouromethane, dichlorotetrafluoroethanol, and 1,1,1,2-tetraflouroethane, or combinations thereof.

Systems of aerosol delivery, such as the pressurized metered dose inhaler and the dry powder inhaler are disclosed in Newman, S. P., Aerosols and the Lung, Clarke, S. W. and Davia, D. editors, pp. 197-22 and can be used in connection with the present invention.

In general, the ketamine is introduced into the subject in the aerosol form in an amount between about 0.01 mg per kg body weight of the mammal up to about 1 mg per kg body weight of said mammal. In a specific embodiment, the dosage is administered as needed. One of ordinary skill in the art can readily determine a volume or weight of aerosol corresponding to this dosage based on the concentration of ketamine in an aerosol formulation of the invention.

The present invention provides liquid aerosol formulations and dosage forms for use in treating subjects suffering from treatment-resistant depression. In general such dosage forms contain ketamine in a pharmaceutically acceptable diluent. Pharmaceutically acceptable diluents in such liquid aerosol formulations include but are not limited to sterile water, saline, buffered saline, dextrose solution, and the like. In a specific embodiment, a diluent that may be used in the present invention or the pharmaceutical formulation of the present invention is phosphate buffered saline or a buffered saline solution generally between the pH 7.0-8.0 range, or water.

The liquid aerosol formulation also may optionally include pharmaceutically acceptable carriers, diluents, solubilizing or emulsifying agents, surfactants and excipients.

The formulation may include a carrier. The carrier is a macromolecule which is soluble in the circulatory system and which is physiologically acceptable where physiological acceptance means that those of skill in the art would accept injection of said carrier into a patient as part of a therapeutic regime. The carrier preferably is relatively stable in the circulatory system with an acceptable plasma half life for clearance. Such macromolecules include but are not limited to Soya lecithin, oleic acid and sorbitan trioleate, with sorbitan trioleate preferred.

The formulations of the present embodiment may also include other agents useful for pH maintenance, solution stabilization, or for the regulation of osmotic pressure. Examples of the agents include but are not limited to salts, such as sodium chloride, or potassium chloride, and carbohydrates, such as glucose, galactose or mannose, and the like.

The present invention further contemplates liquid aerosol formulations comprising ketamine and another therapeutically effective drug, such as a described in further detail below.

It is also contemplated that the present aerosol formulation can be prepared as a dry powder formulation comprising a finely divided powder form of ketamine and a dispersant. For example, the dry powder formulation can comprise a finely divided dry powder containing ketamine, a dispersing agent and also a bulking agent. Bulking agents useful in conjunction with the present formulation include such agents as lactose, sorbitol, sucrose, or mannitol, in amounts that facilitate the dispersal of the powder from the device.

In a further embodiment, an aerosol formulation of the present invention can include other therapeutically or pharmacologically active ingredients in addition to ketamine, such as but not limited to a conventional antidepressant therapies that include, but are not limited to: antidepressants: biogenic amine non-selective reuptake inhibitors, e.g., tricyclic antidepressants like Imipramine; serotonin selective reuptake inhibitors like Fluoxetine (Prozac); monoamine oxidase inhibitors (MAO-I) like phenelezine; other types of antidepressant medications including atypical antidepressants. Antidepressants augmentation with other medications e.g., lithium, T3, T4, etc. Other treatment modalities with antidepressant effects: electro-convulsive treatment (ECT); light therapy psychotherapy e.g., cognitive or interpersonal therapy for depression.

In addition, administration of drugs, reported to ameliorate or exacerbate the symptoms of a neuropsychiatric disorder, include but are not limited to compounds include antidepressants such as lithium salts, carbamazepine, valproic acid, lysergic acid diethylamide (LSD), p-chlorophenylalanine, p-propyidopacetamide dithiocarbamate derivatives e.g., FLA 63; anti-anxiety drugs, e.g., diazepam; monoamine oxidase (MAO) inhibitors, e.g., iproniazid, clorgyline, phenelzine, tranylcypromine, and isocarboxazid; biogenic amine uptake blockers, e.g., tricyclic antidepressants such as desipramine, imipramine and amitriptyline; atypical antidepressants such as mirtazapine, nefazodone, bupropion; serotonin reuptake inhibitors e.g., fluoxetine, venlafaxine, and duloxetine; antipsychotic drugs such as phenothiazine derivatives (e.g., chlorpromazine (thorazine) and trifluopromazine)), butyrophenones (e.g., haloperidol (Haldol)), thioxanthene derivatives (e.g., chlorprothixene), S and dibenzodiazepines (e.g., clozapine); benzodiazepines; dopaminergic agonists and antagonists e.g., L-DOPA, cocaine, amphetamine, a-methyl-tyrosine, reserpine, tetrabenazine, benztropine, pargyline; noradrenergic agonists and antagonists e.g., clonidine, phenoxybenzamine, phentolamine, tropolone. In another embodiment of the treatment methods, the compounds administered comprise compounds, in particular drugs, reported to ameliorate or exacerbate the symptoms of oxidative stress disorder. Such compounds include reduced IS glutathione (GSH), glutathione precursors, e.g., N-acetylcysteine; antioxidants, e.g., vitamins E and C, beta carotene and quinones; inhibitors of lipid membrane peroxidation, e.g., 21-aminosteroid U74006F (tirilazad mesylate), and lazaroids; antioxidants such as mazindol; 2c dizocilpine maleate; selegiline; sulfhydryls N-acetyleysteine and cysteamine; dimethylthiourea; EUK-8 a synthetic, low molecular salen-manganese complex; synthetic manganese-based metalloprotein superoxide dismutase mimic, SC52608; free radical scavengers or suppressors, e.g., pegorgotein, tocotrienol, tocopheral, MDL 74, 18, LY231617, MCI-186, AVS (nicaraven), allopurinol, rifampicin, oxypurinol, hypochlorous acid or recombinant human Cu, Zn-SOD.

Co-administration of ketamine with a second therapeutic agent such as those discussed above is provided in an amount effective to alleviate one or more symptoms of treatment-resistant depression.

The mild adverse effects of ketamine, e.g., dysphoria and/or hallucinations, sometimes called "ketamine dreams," can occur upon administration of a dose of greater than 50 mg of ketamine, and usually require doses greater than 100 mg of ketamine of total dose intranasally. One advantage of the present invention is that nasal delivery of ketamine allows for control of the dose to a level effective for analgesia, but below the level that results in such dreams. However, it is possible that an individual may overdose, particularly in response to an acute episode of depression. Thus, co-administration of a ketamine with the additional exemplary antidepressant agents noted above may be indicated in order to achieve the beneficial anti-depressant effects of ketamine without the side effects of this agent.

In a preferred embodiment, a therapeutically effective amount of the second agent used for the treatment of depression herein is administered in conjunction with ketamine. A therapeutically effective amount of the second agent is an amount effective to alleviate treatment-resistant depression when co-administered with the ketamine.

As shown in the Examples below, patients treated with the intranasal ketamine show remarkable recovery from depression. Such patients may thus end up using decreased amounts of the other antidepressant medications.

As discussed above, the present invention is directed to various methods and compositions for treating treatment-resistant depression comprising intranasal administration of ketamine. In an alternative embodiment, the present invention contemplates intravenous administration of ketamine for the treatment of treatment-resistant depression. Such treatment may be administered alone or may be supplemented with other antidepressant therapies as described herein.

IV administration of ketamine (0.5 mg/kg over 40 minutes) reported improvements in depression within 2 hours post-injection; and continued for up to 1 week. There were no serious adverse events caused by IV administration. Any side effects observed were mild, e.g., euphoria, elevated BP, increased libido, perceptual disturbances, and furthermore these effects abated within 80 min post-infusion. A chronic infusion dosing strategy has been previously described in two patients with depression (Correll et al., Pain Medicine, 7: 92-95. 2006), beginning with IV infusion at 0.1-0.2 mg/kg/hour (15-20 mg/hour). In these cases, dosing was maintained for 5 days, and the endpoint of titration was psychotomimetic side effects. However, there is no report in the literature of a tolerability threshold dose that is maintained for an additional six to nine treatments.

The invention for the first time provides a method of treating treatment-resistant depression comprising intravenous administration of ketamine, wherein the administration is repeated multiple times within a specific time period. For example, the administration is administered at least twice, at least three times, at least four times, at least five time, at least six times, at least seven times, at least eight times, at least nine times, or at least ten times over a period of two to three weeks.

In another alternative embodiment, the administration comprises transdermal administration. Such treatment may be administered alone or may be supplemented with other antidepressant therapies as described herein. Transdermal administration includes passive or active transdermal or transcutaneous modalities, including, for example, patches and iontophoresis devices, as well as topical application of pastes, salves, or ointments.

To date, there are only two published studies of transdermal ketamine, both for use in pain disorder (Vranken et al., Pain., 118:224-31, 2005, Azevedo et al., Anesth Anal., 91: 1479-82, 2000). Neither of these studies provides any teaching of the treatment of depression that is resistant to treatment. Vranken et al. studied the use of an iontophoretic patch (a mechanism of delivery in which the electrically charged drug is transmitted by pulses of galvanic current) in 33 men and women with intractable central neuropathic pain. Vranken et al. chose to use an enantiomer of ketamine, S(+)-ketamine, a compound two times more potent than racemic (which is a mixture of the S(+) and R (+)) (Schuettler et al., Ketamine and its isomers, Textbook of Intravenous Anesthesia. Edited by White P F. Baltimore, Williams & Wilkins, 1997, pp 171-88). Using a randomized, double-blind, placebo-controlled design, subjects were administered either a dose of 50 mg (n=11), 75 mg (n=11), or placebo (n=11), delivered transdermally over 24 hours for 7 days. Vranken et al. found that although there was no change among groups in pain intensity (measure by the Visual Analog Scale), subjects given dose of 75 mg showed significant improvement in pain disability, and subjective physical and mental function. The reported side effects were minimal, with no reports of dissociation or psychotic symptoms. Adverse events included sedation (50 mg, n=3; placebo, n=1), dizziness (50 mg, n=1; placebo, n=3), nausea/vomiting (75 mg, n=1), confusion (50 mg, n=1), vivid dreams (placebo, n=1; 50 mg, n=1) headache (placebo, n=1), and erythema (placebo, n=2). Ketamine blood levels were not measured in this study.

The second study is a randomized, double-blind, placebo-controlled trial using racemic ketamine in a transdermal delivery system (Azevedo et al., 2003). A total of 49 women (ketamine, n=26, placebo, n=23) were studied after abdominal gynecological surgery in which lidocaine epidural blockade was used. Postoperatively, 25 mg is delivered over 24 hrs in decaying quantities (hours 1-4: 1.25 mg/hour; hours 5-8: 0.5 mg/hour; hours 9-24: 0.4 mg/hour). The outcome measure was the time to first rescue analgesic, which was prolonged for ketamine compared to placebo. The subjects reported no side effects from the ketamine, such as nausea or vomiting, confusion, or hallucinations. There is no report of the transdermal administration of ketamine for treating treatment-resistant depression. Similarly, there is no report of transdermal administration of ketamine for treating treatment-resistant depression, wherein the administration is repeated multiple times within a specific time period. For example, the administration is administered at least twice, at least three times, at least four times, at least five time, at least six times, at least seven times, at least eight times, at least nine times, or at least ten times over a period of two to three weeks.

Ketamine is formulated into pharmaceutical compositions comprising a carrier suitable for the desired delivery method. Exemplary carriers include, but are not limited to, any of a number of standard pharmaceutical carriers such as sterile phosphate buffered saline solutions, bacteriostatic water, and the like. A variety of aqueous carriers may be used, e.g., water, buffered water, 0.4% saline, 0.3% glycine and the like.

The compositions of the invention may be designed to be short-acting, fast-releasing, long-acting, or sustained-releasing as described herein. Thus, the pharmaceutical formulations may also be formulated for controlled release or for slow release.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant invention.

The invention also provides a device for patient self-administration of ketamine, which device comprises a transdermal patch containing a ketamine formulation and a pharmaceutically acceptable carrier, wherein the device is formulated to disperse an amount of the ketamine formulation that contains a dose of ketamine effective to alleviate depression.

Those of skill in the art are well aware of general technologies for transdermal drug delivery or administration of a therapeutic agent to the skin. Transdermal drug delivery offers controlled release of a drug to the patient and transdermal patches are user-friendly, convenient, painless, and offer multi-day dosing which usually results in improved patient compliance. In addition, this form of administration of ketamine in the present invention is a particularly useful alternative to intranasal delivery as it is less likely to lead to drug abuse as compared to an intranasal delivery method. The methods of the invention for treating treatment-resistant patients with a transdermal administration of ketamine can include administering ketamine to skin of the face, head or body. Such a ketamine composition can be administered to the skin of the face, scalp, temporal region, arms, stomach, thighs, back, neck and the like. Suitable skin of the face includes skin of the chin, the upper lip, the lower lip, the forehead, the nose, the cheek, the skin around the eyes, the upper eyelid, the lower eyelid or combinations thereof. Suitable skin of the scalp includes the front of the scalp, the scalp over the temporal region, the lateral part of the scalp, or combinations thereof. Suitable skin of the temporal region includes the temple and the scalp over the temporal region and combinations thereof. The ketamine may be formulated into a bioadhesive patch or a bioadhesive strip with an occlusive covering. Alternatively, the transdermal ketamine composition for administration to the skin can be applied as a topical ointment, a topical gel, a lotion, a cream, a solution, a spray, a paint, a film, a foil, a cosmetic, to be applied to the skin in a layer with or without an occlusive dressing.

In addition to transdermal patches, creams lotions and the like, intradermal administration of the ketamine composition also is contemplated. Intradermal administration of a therapeutic agent is defined as within or between the layers of skin. In contrast, subcutaneous administration is defined as beneath the initial layer of skin and intravenous is a systemic administration into the bloodstream. Administration of therapeutic agents by intradermal, intravenous or subcutaneous injection are common means of drug delivery by one skilled in the art.

Once a subject has been treated for depression using the methods of the invention, he/she is monitored for depression symptoms by conventional analysis techniques as described above and such monitoring can be used to adjust the dosage of therapy used.

Example 1

The following examples are included to demonstrate certain embodiments of the invention. It should be appreciated by those of skill in the art that the techniques disclosed in the examples which follow represent techniques discovered by the inventors to function well in the practice of the invention, and thus are considered to constitute certain aspects for its practice. However, those of skill in the art should, in light of the present disclosure, appreciate that many changes can be made in the specific embodiments which are disclosed and still obtain a like or similar result without departing from the spirit and scope of the invention.

Methods

Men and women, ages 18 to 65 years, who were inpatients with a diagnosis of major depressive disorder recurrent without psychotic features as diagnosed by means of the Structured Clinical Interview for Axis I DSM-IV Disorders—Patient Version 28 were eligible to participate. Subjects were required to have a score of ≥18 on the 21-item Hamilton Depression rating (HDRS) [29]) at screening and at start of ketamine/placebo infusion, and to have previously failed at least two adequate antidepressant trials (adequacy of antidepressant trials were determined with the Antidepressant Treatment History Form [30]).

All subjects were in good physical health as determined by medical history, physical exam, blood labs, electrocardiogram, chest x-ray, urinalysis and toxicology. Subjects were free of comorbid substance abuse or dependence for at least 3 months and judged clinically not to be a serious suicidal risk. Comorbid axis I anxiety disorder diagnoses were permitted if they did not require current treatment.

Forty-two subjects were screened and twenty-four subjects were excluded as they did not meet inclusion/exclusion criteria (n=11) or refused to participate (n=13). After a 2 week drug-free period, 18 subjects with DSM-IV major depression were randomized to an intravenous infusion of either ketamine hydrochloride (0.5 mg/kg) or placebo (saline solution) given over 40 minutes with a Baxter infusion pump on 2 test days, a week apart, in a double-blind, crossover study. Seventeen subjects received ketamine and 14 received placebo. Four subjects did not receive placebo after ketamine infusion because they maintained a response for more than 7 days and one subject was discontinued from the study for medical reasons after a placebo infusion.

Subjects were rated 60 minutes prior to the infusion and at 40, 80, 110, and 230 minutes as well as 1, 2, 3, and 7 days after the infusion. The 21-item HDRS, Beck Depression Inventory Scale (BDI; [31]), Brief Psychiatric Rating Scale-positive symptoms (BPRS; [32]), Young Mania Rating Scale (YMRS; [33]), and the visual analogue scales score (VAS-depression; [34]). Raters, who trained together to establish reliability, performed patient ratings. High inter-rater reliability for the HDRS (ICC=0.81) and the YMRS (ICC=0.91) were obtained. Subjects were rated by a separate set of raters to help maintain blind to the infusion procedures and resulting side effects. The first set of raters administered the scales on the day of infusion (60 minutes prior to the infusion and 40, 80, 110 post-infusion). From 230 minutes onwards (days 1 through 7), a separate group of raters rated the subjects. Clinical response was defined as a 50% or greater decrease in the HDRS rating scale from baseline and remission as HDRS<7 [35].

A full factorial, fixed effects linear mixed model with a compound symmetry covariance structure was used to examine the differences between ketamine and placebo over 9 time points from baseline to 7 days. Restricted maximum likelihood estimation was used to estimate missing values. Significant effects were examined with simple effects tests. The 21-item HDRS was the primary outcome measure. Scores from the BDI, BPRS, YMRS, and VAS were secondary outcome measures. Secondary analysis included examination of the individual items of the HDRS. Significance was evaluated at $\alpha<0.05$, two-tailed. Following Shapiro-Wilk's test and visual examination of the data, no cells deviated substantially from normality.

Three sets of linear mixed models were run to fully understand the influence of the active treatment. One set of analysis included only those who completed both phases of the study (completers analysis). Subjects who did not receive both treatment conditions were not included in this analysis. A second set included all available data (intent to treat analysis). Since ratings were made for each day regardless of whether the participants continued in the study, the placebo ratings for the ketamine drop outs appeared to be much lower than would have been expected in an actual placebo phase. A third set of statistics was performed on the first test condition only. In this case the drug effect was a between subjects factor instead of a within subjects factor. Secondary analysis on individual items was performed only with completers.

To evaluate the proportion of responders and remitters at each time point, a McNemar test was used at each time point for the completers and the results were Bonferroni corrected for the number of time points examined.

Carryover was examined using a linear mixed model with the same structures as the primary analysis where drug was a within subjects factor, treatment order was a between subjects factor, and only the baseline measure for each phase was used. The intent to treat sample was used for this analysis since baseline data for both phases was available.

Results

Subject's demographic and clinical characteristics are summarized in Table 1. There were 12 females, and 6 males, and the mean age was 46.7±11.2. Sixty-one percent and 61% had a lifetime comorbid anxiety diagnosis, 39% a lifetime diagnosis of any substance abuse or dependence and 28% a lifetime diagnosis of alcohol abuse or dependence. The mean length of illness was 23.7 years±12.5, the mean duration of the current depressive episode was 33.6 months±37.4, and the mean number of lifetime episodes of depression was 6.6±4.7. The mean number of lifetime antidepressant trials (not including augmentation trials) was 5.7±3.4 and 4 subjects had previously received ECT. All subjects except for one had failed an adequate antidepressant trial for the current major depressive episode.

Using only those who completed both phases of the study, the linear mixed model with the HDRS showed significant main effects for drug ($F=58.24$, $df=1,203$, $p<0.0001$) and time ($F=9.48$, $df=8,203$, $p<0.0001$) and an interaction between drug and time ($F=4.15$, $df=8,203$, $p<0.001$). Simple effects tests indicated significant improvement on ketamine over placebo at 110 minutes through 7 days. The effect size for the drug difference was very large (d=1.46, 95% C.I. 0.91-2.01) after 24 hours and moderate to large (d=0.68, 95% C.I. 0.13-1.23) after 1 week. The percent change in HDRS scores from baseline to day 1 for each subject is listed on Table 1. FIG. 2 shows the generalized least squares means and standard errors for the completer analysis. The intent to treat analysis had similar effects (drug: F=34.08, df=1,260, p<0.0001; time: F=8.92, df=8,257, p<0.0001; drug×time: F=5.29, df=8,257, p<0.0001). Notably, participants were better than placebo within 2 hours (110 minutes) and remained better through 7 days (FIG. 2).

Looking at possible carryover effects with the intent to treat sample, a linear mixed model looking at the baseline measures showed a significant main effect for drug (F=6.25, df=1,16, p=0.02) and a significant interaction (F=5.05, df=1,16, p=0.04), but no main effect for order (F=1.54, df=1,16, p=0.23). Participants who received placebo first had similar baseline measures for the first and second phases (24.4±6.9 vs. 24.9±6.8) (F=0.03, df=1,16, p=0.86), but those who received ketamine first had much lower baselines in the second phase (24.9±6.9 vs. 17.2±6.9) (F=11.80, df=15, p=0.004).

To examine data relatively independent of carryover effects, only the first phase data was used in an additional analysis. Results were similar to those of the completers and intent to treat analysis. There were significant main effects for drug (F=10.44, df=1,16, p=0.005) and time (F=8.25, df=8,126, p<0.0001) and a significant interaction between drug and time (F=4.66, df=1,126, p<0.0001). Scores were lower on ketamine by 80 minutes and the difference remained significant through the seventh day.

Using the completers with the BDI, there were significant main effects for drug (F=50.57, df=1,200, p<0.0001) and time (F=5.82, df=8,200, p<0.0001) and a trend level interaction between drug and time (F=1.90, df=8,200, p=0.06). The patient ratings showed that ketamine seemed to improve depression at 40 minutes through 7 days. Additionally, there were significant changes in the VAS depression scores (drug: F=59.88, df=1,198, p<0.0001; time: F=4.70, df=8,198, p<0.0001; drug×time: F=1.92, df=8,198, p=0.058). Similar to BDI, ketamine improved mood at 40 minutes through 7 days.

On the individual HDRS symptoms, 7 of 20 symptoms had significant time by drug interactions; loss of insight was not tested since none of the participants had this symptom. Depressed mood, guilt, work and interests, and psychic anxiety improved significantly. The earliest improvements were at 40 minutes for depressed mood and guilt. Depersonalization or derealization was worse from 40 to 110 minutes. Motor retardation and gastrointestinal symptoms were worse at 40 minutes, but at day 1 motor retardation was better on ketamine than on placebo. An additional 7 symptoms showed only a significant main effect for drug; symptoms improved on ketamine for suicide, insomnia, general somatic symptoms, genital symptoms, and hypochondriasis. At baseline, no symptoms were different between the ketamine and placebo phases.

Figure 3A:
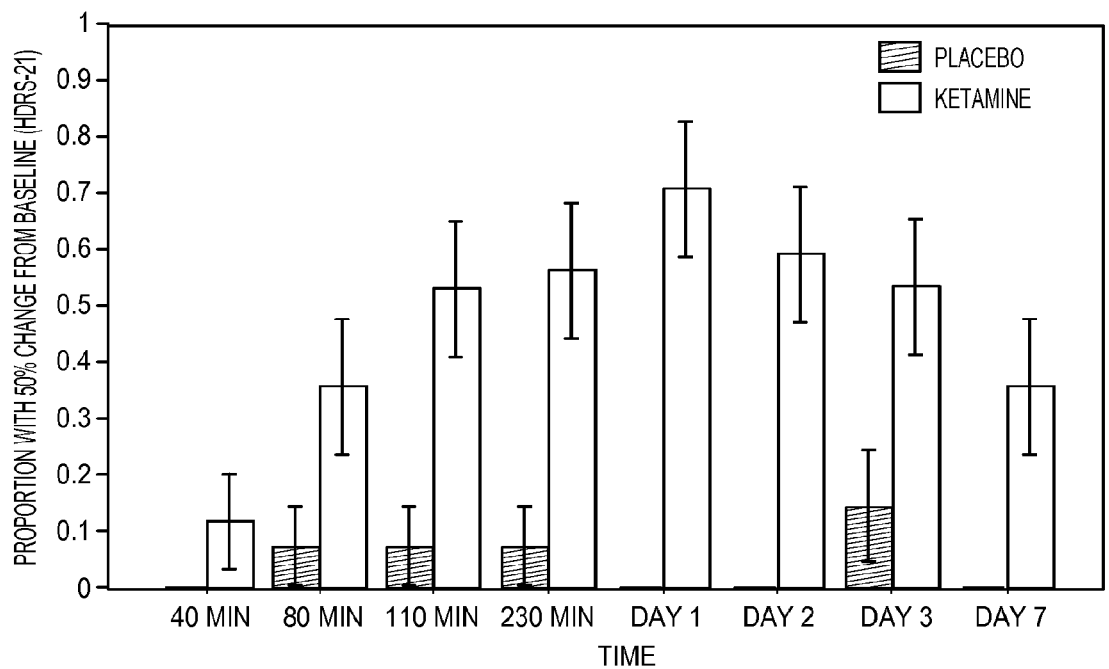
FIG. 3A Portion of responders (50% improvement on HDRS) to ketamine and placebo from minute 40 to day 7 post-infusion (n=18).
Figure 3B:
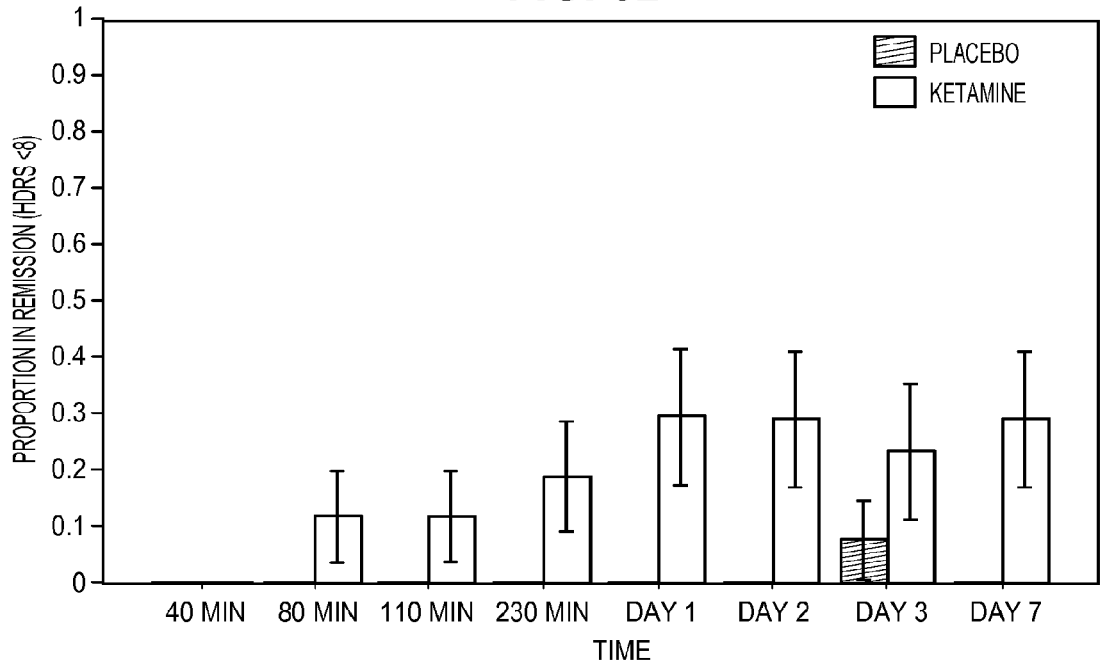
FIG. 3B Portion of remitters (HDRS≤7) to ketamine and placebo from minute 40 to day 7 post-infusion (n=18).

FIG. 3 shows the proportion of responders (FIG. 3A) and remitters (FIG. 3B) at each time point for the intent to treat sample. One day after infusion 12 of the 17 (71%) subjects treated with ketamine met response criteria as compared to 0 of 14 (0%) on placebo. Five of 17 (29%) on ketamine met remission criteria one day after infusion, while none (0%) reached remission on placebo at the same time point. Six (35%) subjects maintained response to ketamine for at least 1 week; 2 of these maintained response at least 2 weeks. By contrast, no subject on placebo responded at 1 or 7 days. For completers, McNemar tests showed significantly more responders to ketamine on day 1 and 2, but after Bonferroni correction, only day 1 was significant. The number of remitters was not significant at any time point.

BPRS positive symptoms [35, 34] were worse on ketamine than placebo only at 40 minutes (drug: F=4.23, df=1,200, p=0.04; time: F=9.31, df=8,200, p<0.0001; drug× time: F=6.89, df=8,200, p<0.0001) (FIG. 2). Similarly, YMRS scores were worse (higher score) on ketamine than placebo at 40 minutes only, but they were significantly better from days 1 to 2 (drug: F=3.08, df=1,201, p=0.08; time: F=3.54, df=8,201, p<0.001; drug×time: F=4.68, df=8,201, p<0.0001) (FIG. 2).

There was a trend for an inverse relationship between the percent change in HDRS at day 1 and the peak percent change in BPRS positive symptoms (r=−0.46, p=0.06). None of the other factors listed in table 1 predicted a response to ketamine.

Adverse Events: Side effects occurring more commonly on ketamine than placebo were perceptual disturbances, confusion, elevations in blood pressure, euphoria, dizziness, and increased libido. Side effects occurring more frequently with placebo than ketamine were gastrointestinal distress, increased thirst, headache, metallic taste, and constipation. The majority of these side effects ceased within 80 minutes after the infusion. In no case did euphoria or derealization/depersonalization persist beyond 110 minutes (FIG. 2). No serious adverse events occurred during the study.

Discussion

The present invention provides a robust, rapid (hours) and relatively sustained (1 week) response to a single-dose of the NMDA antagonist ketamine. Improvement in mood ratings for the course of the week was greater with ketamine than placebo; this difference was statistically significant for the 21-HDRS (from 110 minutes through 7 days) and self-rated BDI (from 40 minutes through 7 days). To our knowledge, there has never been a report of any other drug or somatic treatment (i.e., sleep deprivation, thyrotropin-releasing hormone, antidepressant, dexamethasone, or electroconvulsive therapy [ECT]) [36, 39, 40, 41, 42] that results in such a dramatic rapid and prolonged response with a single administration. In reviews of antidepressant trials in major depression response rates at week 8 were for bupropion 62%, SSRI 63%, and venlafaxine 65% [37, 38, 42]. In the present study involving treatment-resistant subjects, these response rates were obtained the day after the ketamine infusion.

In contrast to the dramatic effects observed in this study, a previous controlled study did not show the low- to moderate-affinity non-competitive NMDA antagonist memantine, administered orally, to have antidepressants effects [63, 38]. While it is likely that higher affinity NMDA antagonists are necessary for antidepressant effects to occur, it must be acknowledged that the intravenous administration may also be an important factor.

It is possible that higher affinity NMDA antagonists are necessary to induce antidepressant effects. Ketamine in contrast to memantine has (a) higher affinity for the NMDA receptor, (b) much slower open channel blocking/unblocking kinetics, (c), a different type of channel closure (i.e., 'trapping block' as opposed to 'partial trapping' properties), [44, 63] and (d) different NMDA subunit selectivity [64, 65, 66]. Such differences might explain the antidepressant properties observed with ketamine in the present trial.

When comparing our results with the preliminary study by Berman et al., [27] we confirmed the finding of rapid antidepressant response with ketamine. The larger sample size of our study permitted us to obtain additional information regarding the time of onset, course of response and degree of improvement with ketamine. Compared to the previous study, we were able to (a) detect an earlier onset of antidepressant effect (110 minutes by objective ratings and 40 minutes by self-report, post-infusion vs. 230 minutes) after infusion; (b) find a more prolonged antidepressant effect of ketamine which remained significant up to 7 days post-infusion (the previous study collected ratings only until day 3); and (c) better characterize the magnitude of response and remission obtained over the course of 7 days. The Berman et al., study group reported that 4 of 8 patients obtained a 50% or greater decreases in HDRS during the 3-day follow-up period. In our study, we found 71% response and 29% remission rates on day 1 (FIGS. 2, 3) and 35% of subjects were able to maintain response for at least 1 week. The relatively prolonged antidepressant effect that occurred with ketamine (~1 week) is remarkable considering its short half-life which is approximately 2 hours for ketamine [67] and 5 hours for norketamine; the latter metabolite is 7-10 times less potent than ketamine [68]. Blood levels of ketamine or its metabolites were not collected in this study. As a result, this study cannot rule out the possibility that differences in drug metabolism may have contributed in part to the current findings.

It should be noted that although these results are provocative, they may not be generalizable to all depressed populations. The subjects in this study were a refractory subgroup who were relatively late in their course of illness (Table 1), and as such, their neurobiology and pharmacological responses may be different from those with a less severe or shorter course of illness.

Several factors need to be considered in interpreting these data. Although the sample size was relatively small, three different types of analysis showed significance of ketamine over placebo, and the effect sizes of this study were very large at day 1 and moderate to large at day 7. Consistent with all of the published randomized placebo-controlled studies with ketamine, we also found short-lived perceptual disturbances [26, 27, 44, 45, 46, 64]; it has to be acknowledged that such symptoms could have affected study blind. Hence, limitations in preserving study blind may have biased patient reporting by diminishing placebo effects, thereby potentially confounding results. One potential study design in future studies with ketamine might be to include an active comparator such as intravenous amphetamine (a dopamine agonist) which also produces psychotogenic effects [77].

However, the time of onset and course of antidepressant response (relatively prolonged) after receiving only one dose of ketamine was nearly identical for each subject; this pattern suggests that there was indeed, a true drug effect. The improvement associated with ketamine infusion reflects a lessening of core symptoms of depression and is disconnected from ketamine-induced euphoria and psychotomimetic symptoms. In support, the antidepressant effect of ketamine became significant in the HDRS scale at 110 minutes after a return of BPRS positive and YMRS scores to baseline (FIG. 2). However, although BPRS positive scores returned to baseline within 110 minutes, the change in BPRS positive symptoms from baseline to the 110 minute time point trended to predict a greater percent change (decrease) in HDRS scores at day 1. As a result, future research should explore a wider range of ketamine doses and rates of administration, and determine if the presence or intensity of euphoric or psychomimetic effects are necessary for rapid antidepressant effects to occur. The dose of 0.5 mg/kg chosen for the present study is reported to be sufficient to test the validity of the concept of the NMDA receptor antagonism with ketamine. The dose of ketamine used in our study was based on 1) in vitro data of NMDA blockade, 2) its mood enhancing effects in healthy volunteers and 3) its antidepressant effects in a pilot study of patients with major depression [27, 46].

While ketamine is believed to be relatively selective for NMDA receptors, the possibility that these intriguing results are mediated by interactions with other receptors cannot entirely be ruled out [65, 69]. However, ketamine binds to the NMDA receptor with an affinity that is several fold higher than that for other sites, [70, 71, 72, 73] and behaviors induced by NMDA receptor antagonists are not blocked by opiate, cholinergic, or monoamine receptor antagonists [74], providing indirect evidence that ketamine's behavioral effects are mediated by its interaction with the phenylcyclidine (PCP) site. In vitro studies have found that ketamine only reduces non-NMDA voltage-gated potassium currents at much higher than reported in patients anesthetized with ketamine [75]. This suggests that low doses of ketamine enhance selectivity for the PCP site. Nevertheless, more selective NMDA antagonists will need to be tested in patients with major depression. Several NR2B subunit-selective antagonists are currently being developed for ischemic brain injury [76].

In conclusion, the results of the present study support the hypothesis that directly targeting the NMDA receptor complex may bring about rapid and relatively sustained antidepressant effects. This line of research suggests a novel avenue holds considerable promise for developing new treatments for depression that have the potential to alleviate much of the morbidity and mortality associated with the delayed onset of action of traditional antidepressants. Those of skill can now use the studies described herein to develop strategies for maintaining the rapid antidepressant response obtained with ketamine in long-term therapy.

Example 2

Repeated Administration of a Fixed Dose IV Ketamine

The following example describes a treatment strategy for treatment-resistant depression involving the repeated administration of ketamine for rapid mood stabilization.

A fixed TV ketamine dose (0.5 mg/kg infusion over 40 minutes) is repeated for up to six to nine sessions over a two to three week period in hospital. The determination of the number of treatment sessions is based on clinical response and tolerability. Standard pharmacotherapy treatments would be initiated in hospital such that once the final ketamine treatment session is completed; the patient has achieved a therapeutic dosage of an antidepressant for relapse prevention.

Example 3

Repeated Administration of a Continuation Dose of IV Ketamine

The following example describes another treatment strategy for treatment-resistant depression involving the repeated administration of a continuation dose of ketamine for rapid mood stabilization.

All patients would initiate IV ketamine at the dose of 0.5 mg/kg at a rate of 1 mg/min, with continued titration over 40 minutes based on tolerability. At the first treatment, a tolerability threshold is determined using an empirical titration procedure based on the presence of psychotic side effects. he individualized optimal tolerated dose would serve as the continuation dosage for repeated treatments as described in Example 2 above. For patients who respond to IV ketamine at the 24 hour assessment, the continuation dose would be 20% reduced from the dose associated with psychotic side effects. If a patient did not have any psychotic side effects and is a responder at 24 hours, then the standard dose of 0.5 mg/kg is continued for the repeated dose phase.

Example 4

Transdermal Administration of Ketamine

The following example describes treatment strategies for treatment-resistant depression involving transdermal administration of ketamine for rapid mood stabilization.

Another potential route of administration of ketamine is the use of a transdermal patch. Patients would be given a patch comprising a reasonable starting dose for depression as described in Azevedo et al 2003 (25 mg patch over 24 hours). For repeated dosing administration, a patch will be administered six-nine times over a two to three week period. The determination of the number of treatment sessions is based on clinical response and tolerability.

All of the above U.S. patents, U.S. patent application publications, U.S. patent applications, foreign patents, foreign patent applications and non patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention.

TABLE 1

Demographic, and Clinical Characteristics

| Number | Age, yrs | Gender | Length of illness, yrs | Current Episode, mo | Number of previous episodes | Failed medication and somatic treatments |
|---|---|---|---|---|---|---|
| 1 | 43 | F | 24 | 4 | 10 | SSRI (2); MAOI; AAP (2); BZD (3) |
| 2 | 46 | M | 29 | 144 | 2 | SSRI (3); SNRI; Bup; OAD (4) AAP; Lam; Sti; BZD |
| 3 | 35 | F | 20 | 11 | 20 | SSRI; Bup; TCA; OAD (2); AAP; Lam; BZD(3) |
| 4 | 43 | F | 24 | 24 | 4 | SSRI (3); SNRI; Bup; OAD (2); Li; Lam; Sti (2) |
| 5 | 45 | F | 27 | 9 | 1 | SSRI (3); BZD |
| 6 | 56 | F | 38 | 24 | 10 | SSRI (3); Bup; TCA (2); VPA; BZD (2) |
| 7 | 57 | F | 44 | 60 | 9 | SSRI (3); Bup MAOI; OAD (2); AAP (3); Li; Lam; Sti; BZD (3); ECT |
| 8 | 19 | F | 3 | 8 | 4 | SSRI (3); Bup; Sti |
| 9 | 48 | F | 33 | 60 | 9 | SSRI (4); Bup; OAD; VPA; Sti; BZD |
| 10 | 45 | M | 14 | 1 | 6 | SSRI (4); TCA; OAD (3); Sti; BZD (3); ECT |
| 11 | 28 | M | 16 | 17 | 4 | SSRI (2); SNRI; TCA; OAD; AAP (2); Li; Lam; BZD (3) |
| 12 | 46 | F | 13 | 4 | 9 | SSRI (2); Bup; TCA (2) |
| 13 | 55 | M | 22 | 4 | 9 | SSRI (2); Bup; AAP; Li; BZD; (2) |
| 14 | 62 | F | 6 | 12 | 4 | SSRI (3); OAD (2); BZD |
| 15 | 60 | F | 47 | 55 | 3 | SSRI (2); TCA; BZD (2) |
| 16 | 59 | M | 7 | 84 | 3 | SSRI (2) |
| 17 | 50 | M | 31 | 60 | 3 | SSRI (4); Bup; TCA (3); MAOI; OAD (7); VPA; Sti (3); BZD; AAP; Li; ECT |
| 18 | 44 | F | 29 | 24 | 10 | SSRI; SNRI; TCA; OAD; AAP; Sti; ECT |
| Group | 46.7 ± 11.2 | 12 F/6 M | 23.7 ± 12.5 | 33.6 ± 37.4 | 6.6 ± 4.7 | 5.7 ± 3.4*† |

| Number | Lifetime diagnosis of any substance abuse or dependence# | Lifetime diagnosis of alcohol abuse or dependence | Peak change in BPRS positive symptoms on Ketamine | % Change in HDRS (day 1) Ketamine | % Change in HDRS (day 1) Placebo |
|---|---|---|---|---|---|
| 1 | No | No | +9 | −90% | N/A |
| 2 | No | No | +2 | −85% | −15% |
| 3 | Yes | No | +5 | −78% | N/A |
| 4 | No | No | +7 | −78% | +11% |
| 5 | Yes | Yes | −1 | −74% | +14% |
| 6 | Yes | Yes | +7 | −64% | −18% |
| 7 | Yes | Yes | +3 | −61% | 0% |
| 8 | No | No | 0 | −57% | −27% |
| 9 | Yes | No | +8 | −55% | N/A |
| 10 | Yes | Yes | +2 | −54% | +25% |

TABLE 1-continued

Demographic, and Clinical Characteristics

| | | | | | |
|---|---|---|---|---|---|
| 11 | No | No | −1 | −50% | −41% |
| 12 | No | No | +6 | −50% | 0% |
| 13 | No | No | −2 | 39% | N/A |
| 14 | No | No | +3 | −39% | −10% |
| 15 | No | No | +1 | −36% | −26% |
| 16 | No | No | +3 | −29% | −35% |
| 17 | No | No | +1 | −17% | −20% |
| 18 | Yes | Yes | N/A | N/A | +8% |
| Group | 7 Yes/11 No | 5 Yes/13 No | +3.1 ± 3.4 | −56.2 ± 20.4% | −9.8 ± 20.1% |

Abbreviations: AAP, atypical antipsychotic; BZD, benzodiazepine; Bup, buproprion; ECT, electroconvulsive therapy; HDRS, Hamilton depression rating scale; Lam, lamictal; Li, lithium; MAOI, monoamine oxidase inhibitor; OAD, other antidepressants (e.g. nefazodone, trazodone, pramipexole, etc); SNRI, selective norepinephrine reuptake inhibitor; SSRI, selective serotonin reuptake inhibitor; TCA, tricyclic antidepressants; VPA, depakote; Sti, stimulant; #lifetime substance abuse/column also includes subjects with lifetime alcohol abuse/dependence;
*number of antidepressant trials not including augmentation strategies;
†All subjects except for one had failed an adequate antidepressant trial for the current depressive episode;
"−" indicates a decrease in HDRS scores (improvement of depression) and
"+" indicates an increase in HDRS scores (worsening of depression).

All of the compositions and/or methods disclosed and claimed herein can be made and executed without undue experimentation in light of the present disclosure. While the compositions and methods of this invention have been described in terms of specific embodiments, it will be apparent to those of skill in the art that variations of the compositions and/or methods and in the steps or in the sequence of steps of the method described herein can be made without departing from the concept, spirit and scope of the invention. More specifically, it will be apparent that certain agents which are both chemically and physiologically related may be substituted for the agents described herein while the same or similar results are achieved. All such similar substitutes and modifications apparent to those skilled in the art are deemed to be within the spirit, scope and concept of the invention as defined by the appended claims.

The references cited herein throughout, to the extent that they provide exemplary procedural or other details supplementary to those set forth herein, are all specifically incorporated herein by reference. At certain points throughout the specification, references are referred to using an number in square brackets. Those numbers correspond to the following list of references, each of which is incorporated herein by reference:

1. Kessler R C, Berglund P, Demler O, Jin R, Merikangas K R, Walters EE. Lifetime prevalence and age-of-onset distributions of DSM-IV disorders in the National Comorbidity Survey Replication. Arch Gen Psychiatry. June 2005; 62(6):593-602.
2. Murray C J, Lopez A D. Global mortality, disability, and the contribution of risk factors: Global Burden of Disease Study. Lancet. May 17, 1997; 349(9063):1436-1442.
3. Jick H, Kaye J A, Jick SS. Antidepressants and the risk of suicidal behaviors. Jama. Jul. 21 2004; 292(3):338-343.
4. Hyman S E, Nestler E J. Initiation and adaptation: a paradigm for understanding psychotropic drug action. Am J. Psychiatry. February 1996; 153(2):151-162.
5. Manji H K, Quiroz J A, Sporn J, et al. Enhancing neuronal plasticity and cellular resilience to develop novel, improved therapeutics for difficult-to-treat depression. Biol Psychiatry. Apr. 15 2003; 53(8):707-742.
6. Sapolsky R M. Is impaired neurogenesis relevant to the affective symptoms of depression? Biol Psychiatry. Aug. 1 2004; 56(3):137-139.
7. D'Sa C, Duman R S. Antidepressants and neuroplasticity. Bipolar Disord. June 2002; 4(3):183-194.
8. Duman R S. Synaptic plasticity and mood disorders. Mol Psychiatry. 2002; 7 Suppl 1:S29-34.
9. Skolnick P. Antidepressants for the new millennium. Eur J. Pharmacol. Jun. 30 1999; 375(1-3):31-40.
10. Skolnick P, Layer R T, Popik P, Nowak G, Paul I A, Trullas R. Adaptation of N-methyl-D-aspartate (NMDA) receptors following antidepressant treatment: implications for the pharmacotherapy of depression. Pharmacopsychiatry. January 1996; 29(1):23-26.
11. Skolnick P. Modulation of glutamate receptors: Strategies for the development of novel antidepressants. Amino Acids. 2002; 23(1-3):153-159.
12. Zarate C A, Jr., Du J, Quiroz J, et al. Regulation of Cellular Plasticity Cascades in the Pathophysiology and Treatment of Mood Disorders: Role of the Glutamatergic System. Ann N Y Acad Sci. November 2003; 1003:273-291.
13. Layer R T, Popik P, Olds T, Skolnick P. Antidepressant-like actions of the polyamine site NMDA antagonist, eliprodil (S L-82.0715). Pharmacol Biochem Behav. November 1995; 52(3):621-627.
14. Meloni D, Gambarana C, De Montis M G, Dal Pra P, Taddei I, Tagliamonte A. Dizocilpine antagonizes the effect of chronic imipramine on learned helplessness in rats. Pharmacol Biochem Behav. October 1993; 46(2):423-426.
15. Moryl E, Danysz W, Quack G. Potential antidepressive properties of amantadine, memantine and bifemelane. Pharmacol Toxicol. June 1993; 72(6):394-397.
16. Papp M, Moryl E. Antidepressant activity of non-competitive and competitive NMDA receptor antagonists in a chronic mild stress model of depression. Eur J. Pharmacol. Sep. 22 1994; 263(1-2):1-7.
17. Przegalinski E, Tatarczynska E, Deren-Wesolek A, Chojnacka-Wojcik E.
Antidepressant-like effects of a partial agonist at strychnine-insensitive glycine receptors and a competitive NMDA receptor antagonist. Neuropharmacology. January 1997; 36(1):31-37.
18. Trullas R, Skolnick P. Functional antagonists at the NMDA receptor complex exhibit antidepressant actions. Eur J. Pharmacol. Aug. 21 1990; 185(1):1-10.
19. Yilmaz A, Schulz D, Aksoy A, Can beyli R. Prolonged effect of an anesthetic dose of ketamine on behavioral despair. Pharmacol Biochem Behav. January-February 2002; 71(1-2):341-344.
20. Boyer P A, Skolnick P, Fossom L H. Chronic administration of imipramine and citalopram alters the expression of NMDA receptor subunit mRNAs in mouse brain. A quantitative in situ hybridization study. J Mol Neurosci. June 1998; 10(3):219-233.

21. Krystal J H, Sanacora G, Blumberg H, et al. Glutamate and GABA systems as targets for novel antidepressant and mood-stabilizing treatments. Mol Psychiatry. 2002; 7 Suppl 1:S71-80.

22. Zarate C A, Quiroz J, Payne J, Manji H K. Modulators of the glutamatergic system: implications for the development of improved therapeutics in mood disorders. Psychopharmacol Bull. Autumn 2002; 36(4):35-83.

23. Sanacora G, Gueorguieva R, Epperson C N, et al. Subtype-specific alterations of gamma-aminobutyric acid and glutamate in patients with major depression. Arch Gen Psychiatry. July 2004; 61(7):705-713.

24. Calabrese J R, Bowden C L, Sachs G S, Ascher J A, Monaghan E, Rudd G D. A double-blind placebo-controlled study of lamotrigine monotherapy in outpatients with bipolar I depression. Lamictal 602 Study Group. J Clin Psychiatry. February 1999; 60(2):79-88.

25. Zarate CAJ, Payne J L, Quiroz J, et al. An Open-Label Trial of Riluzole in Treatment-Resistant Major Depression. Am J. Psychiatry. 2004; 161:171-174.

26. Zarate CAJ, Quiroz J A, Singh J B, et al. An open-label trial of the glutamate-modulating agent riluzole in combination with lithium for the treatment of bipolar depression. Biol Psychiatry. 2005; 57:430-432.

27. Berman R M, Cappiello A, Anand A, et al. Antidepressant effects of ketamine in depressed patients. Biol Psychiatry. Feb. 15 2000; 47(4):351-354.

28. First M B, Spitzer R L, Gibbon M, Williams A R. Structured Clinical Interview for DSM-I V T R Axis I Disorders, Research Version, Patient Edition (SCID-IJP). New York: New York State Psychiatric Institute, Biometrics Research; 2001.

29. Hamilton M. A rating scale for depression. J Neurol Neurosurg Psychiatry. 1960; 23:56-62.

30. Sackeim H A. The definition and meaning of treatment-resistant depression. J Clin Psychiatry. 2001; 62 Suppl 16:10-17.

31. Beck A T, Beamesderfer A. Assessment of depression: the depression inventory. Mod Probl Pharmacopsychiatry. 1974; 7(0):151-169.

32. Overall J E, Gorham D R. The Brief Psychiatric Rating Scale. Psychol Rep. 1962; 10:799-812. 33. Young R C, Biggs J T, Ziegler V E, Meyer D A. A rating scale for mania: reliability, validity and sensitivity. Br J. Psychiatry. November 1978; 133:429-435.

34. Aitken R C. Measurement of feelings using visual analogue scales. Proc R Soc Med. October 1969; 62(10): 989-993.

35. Frank E, Prien R F, Jarrett R B, et al. Conceptualization and rationale for consensus definitions of terms in major depressive disorder. Remission, recovery, relapse, and recurrence. Arch Gen Psychiatry. September 1991; 48(9):851-855.

36. Kane J M, Marder S R, Schooler N R, et al. Clozapine and haloperidol in moderately refractory schizophrenia: a 6-month randomized and double-blind comparison. Arch Gen Psychiatry. October 2001; 58(10):965-972.

37. Entsuah A R, Huang H, Thase M E. Response and remission rates in different subpopulations with major depressive disorder administered venlafaxine, selective serotonin reuptake inhibitors, or placebo. J Clin Psychiatry. November 2001; 62(11):869-877.

38. Thase M E, Haight B R, Richard N, et al. Remission rates following antidepressant therapy with bupropion or selective serotonin reuptake inhibitors: a meta-analysis of original data from 7 randomized controlled trials. J Clin Psychiatry. August 2005; 66(8):974-981.

39. Wirz-Justice A, Van den Hoofdakker R H. Sleep deprivation in depression: what do we know, where do we go? Biol Psychiatry. Aug. 15 1999; 46(4):445-453.

40. Husain MM, Rush A J, Fink M, et al. Speed of response and remission in major depressive disorder with acute electroconvulsive therapy (ECT): a Consortium for Research in ECT (CORE) report. J Clin Psychiatry. April 2004; 65(4):485-491.

41. Marangell L B, George M S, Callahan A M, et al. Effects of intrathecal thyrotropin-releasing hormone (protirelin) in refractory depressed patients. Arch Gen Psychiatry. March 1997; 54(3):214-222.

42. DeBattista C, Posener J A, Kalehzan B M, Schatzberg A F. Acute antidepressant effects of intravenous hydrocortisone and CRH in depressed patients: a double-blind, placebo-controlled study. Am J. Psychiatry. August 2000; 157 (8):1334-1337.

43. Drevets W C, Gautier C, Price J C, et al. Amphetamine-induced dopamine release in human ventral striatum correlates with euphoria. Biol Psychiatry. Jan. 15 2001; 49(2):81-96.

44. Bolshakov K V, Gmiro V E, Tikhonov D B, Magazanik L G. Determinants of trapping block of N-methyl-d-aspartate receptor channels. J. Neurochem. October 2003; 87(1):56-65.

45. Anand A, Charney D S, Oren D A, et al. Attenuation of the neuropsychiatric effects of ketamine with lamotrigine: support for hyperglutamatergic effects of N-methyl-D-aspartate receptor antagonists. Arch Gen Psychiatry. March 2000; 57(3):270-276.

46. Krystal J H, Karper L P, Seibyl J P, et al. Subanesthetic effects of the noncompetitive NMDA antagonist, ketamine, in humans. Psychotomimetic, perceptual, cognitive, and neuroendocrine responses. Arch Gen Psychiatry. March 1994; 51(3):199-214. 21

47. Carr D B, Goudas L C, Denman W T, et al., Safety and efficacy of intranasal ketamine for the treatment of breakthrough pain in patients with chronic pain: a randomized, double-blind, placebo-controlled, crossover study, Pain 2004; 108: 17-27

48. Trivedi M H, Rush A J, Wisniewski S R et al., Evaluation of outcomes with citalopram for depression using measurement-based care in STAR*D: implications for clinical practice, Am J. Psychiatry. 2006 January; 163(1): 28-40

49. Keller M B, Issues in treatment-resistant depression, J Clin Psychiatry. 2005; 66(8):5-12

50. Louon A, Lithander J, Reddy V G, Gupta A., Sedation with nasal ketamine and midazolam for cryotherapy in retinopathy of prematurity, Br J. Ophthalmol. 1993 August; 77(8):529-30;

51. Weksler N, Ovadia L, Muati G, Stay A., Nasal ketamine for paediatric premedication, Can J. Anaesth. 1993 February; 40(2):119-21

52. Fava M., Diagnosis and definition of treatment-resistant depression, Biol Psychiatry. 2003 Apr. 15; 53(8):649-59

53. Rush A J, Thase M E, Dube S., Research issues in the study of difficult-to-treat depression, Biol Psychiatry. 2003 Apr. 15; 53(8):743-53

54. Sackeim H A, Rush A I, George M S, et al., Vagus nerve stimulation (VNS) for treatment-resistant depression: efficacy, side effects, and predictors of outcome, Neuropsychopharmacology. 2001 November; 25(5):713-28

55. Thase M E, Rush A J., When at first you don't succeed: sequential strategies for antidepressant nonresponders J Clin Psychiatry. 1997; 58 Suppl 13:23-9.

56. Domino E F, Chodoff P, Corssen G. Pharmacologic effects of ci-581, a new dissociative anesthetic, in man Clin Pharmacol Ther. 1965 May-June; 40:279-91);

57. Bovill J G, and Dundee J W., Alterations in response to somatic pain associated with anaesthesia. XX. Ketamine, Br J. Anaesth. 1971 May; 43(5):496-9

58 Sadove M S, Shulman M, Hatano S, Fevold N. Analgesic effects of ketamine administered in subdissociative doses, Anesth Analg. 1971 May-June; 50(3):452-7

59 Oshima E, Tei K, Kayazawa H, Urabe N., Continuous subcutaneous injection of ketamine for cancer pain Can J. Anaesth. 1990 April; 37(3):385-6

60. Stannard C F, Porter G E. Ketamine hydrochloride in the treatment of phantom limb pain, Pain. 1993 August; 54(2):227-30

61. Goodwin, et al., 1990, Manic Depressive Illness, Oxford University Press, New York.

62. Hedlung, et al. The Hamilton Rating Scale for Depression, Journal of Operational Psychiatry (1979) 10 (2) 149-165

63. Zarate CAJ, Singh J, Quiroz J, et al. A double-blind placebo-controlled study of memantine in major depression. Am J. Psychiatry. January 2006; 163(1):153-5.

64. Narita M, Yoshizawa K, Nomura M, Aoki K, Suzuki T. Role of the NMDA receptor subunit in the expression of the discriminative stimulus effect induced by ketamine. Eur J. Pharmacol. Jun. 29 2001; 423(1):41-46.

65. De Vry J, Jentzsch K R. Role of the NMDA receptor NR2B subunit in the discriminative stimulus effects of ketamine. Behav Pharmacol. May 2003; 14(3):229-235.

66. Maier J M, Esselmann H, Wiltfang J, et al. Memantine inhibits ethanol-induced NMDA receptor up-regulation in rat hippocampal neurons. Brain Res. Aug. 9 2005; 1052(2): 156-162.

67. White P F, Schuttler J, Shafer A, Stanski D R, Horai Y, Trevor A J. Comparative pharmacology of the ketamine isomers. Studies in volunteers. Br J. Anaesth. February 1985; 57(2):197-203.

68. Newcomer J W, Farber N B, Jevtovic-Todorovic V, et al. Ketamine-induced NMDA receptor hypofunction as a model of memory impairment and psychosis. Neuropsychopharmacology. February 1999; 20(2):106-118.

69. Kapur S, Seeman P. Ketamine has equal affinity for NMDA receptors and the high-affinity state of the dopamine D2 receptor. Biol Psychiatry. Jun. 1 2001; 49(11):954-957.

70. Hustveit 0, Maurset A, Oye I. Interaction of the chiral forms of ketamine with opioid, phencyclidine, sigma and muscarinic receptors. Pharmacol Toxicol. December 1995; 77(6):355-359.

71. Smith D J, Azzaro A J, Zaldivar S B, Palmer S, Lee H S. Properties of the optical isomers and metabolites of ketamine on the high affinity transport and catabolism of monoamines. Neuropharmacology. April 1981; 20(4):391-396.

72. Lindefors N, Barati S, O'Connor W T. Differential effects of single and repeated ketamine administration on dopamine, serotonin and GABA transmission in rat medial prefrontal cortex. Brain Res. Jun. 13 1997; 759(2):205-212.

73. Elliott K, Kest B, Man A, Kao B, Inturrisi C E. N-methyl-D-aspartate (NMDA) receptors, mu and kappa opioid tolerance, and perspectives on new analgesic drug development. Neuropsychopharmacology. December 1995; 13(4):347-356.

74. Byrd L D, Standish L J, Howell LL. Behavioral effects of phencyclidine and ketamine alone and in combination with other drugs. Eur J. Pharmacol. Dec. 15 1987; 144(3): 331-341.

75. Rothman S. Noncompetitive N-methyl-D-aspartate antagonists affect multiple ionic currents. J Pharmacol Exp Ther. July 1988; 246(1):137-142.

76. Wang C X, Shuaib A. NMDA/NR2B selective antagonists in the treatment of ischemic brain injury. Curr Drug Targets CNS Neurol Disord. April 2005; 4(2):143-151.

77. Krystal J H, Perry E B, Jr., Gueorguieva R, et al. Comparative and interactive human psychopharmacologic effects of ketamine and amphetamine: implications for glutamatergic and dopaminergic model psychoses and cognitive function. Arch Gen Psychiatry. September 2005; 62(9): 985-994.

78. Krystal J H, Perry E B Jr, Gueorguieva R, Belger A, Madonick S H, et al., Comparative and interactive human psychopharmacologic effects of ketamine and amphetamine: implications for glutamatergic and dopaminergic model psychoses and cognitive function. Arch Gen Psychiatry. 2005; 62(9):985-94.

79. Krystal J H, Abi-Saab W, Perry E, D'Souza D C, et al., Preliminary evidence of attenuation of the disruptive effects of the NMDA glutamate receptor antagonist, ketamine, on working memory by pretreatment with the group II metabotropic glutamate receptor agonist, L Y354740, in healthy human subjects, Psychopharmacology (Berl). 2005; 179(1): 303-9.

80. Krystal J H, D'Souza D C, Karper L P, Bennett A, Abi-Dargham A, et al.,

Interactive effects of subanesthetic ketamine and haloperidol in healthy humans., Psychopharmacology (Berl). 1999; 145(2):193-204.

81. Krystal J H, Karper L P, Bennett A, D'Souza D C, Abi-Dargham A, et al., Interactive effects of subanesthetic ketamine and subhypnotic lorazepam in humans. Psychopharmacology (Berl). 1998; 135(3):213-29.

82. Wanna 0, Werawatganon T, Piriyakitphaiboon S, Taesiri B., A comparison of propofol and ketamine as induction agents for cesarean section. J Med Assoc That. 2004; 87(7):774-9.

83 Bonanno F G., Ketamine in war/tropical surgery (a final tribute to the racemic mixture). Injury. 2002; 33(4): 323-7.

84. McLean R F, Baker A J, Walker S E, Mazer C D, Wong B I, Harrington E M.,

Ketamine concentrations during cardiopulmonary bypass. Can J. Anaesth. 1996; 43(6):580-4.

85. Marlow R, Reich D L, Neustein S, Silvay G., Haemodynamic response to induction of anaesthesia with ketamine/midazolam. Can J. Anaesth. 1991; 38(7):844-8.

86. Gutzke G E, Shah K B, Glisson S N, Griesemer R W, Kleinman B S, et al., Cardiac transplantation: a prospective comparison of ketamine and sufentanil for anesthetic induction. J Cardiothorac Anesth. 1989; 3(4):389-95.

87. Vranken J H, Dijkgraaf M G, Kruis M R, van Dasselaar N T, van der Vegt M H. Iontophoretic administration of S(+)-ketamine in patients with intractable central pain: a placebo-controlled trial. Pain. 2005 November; 118 (1-2):224-31.

88. Azevedo V M, Lauretti G R, Pereira N L, Reis M P. Transdermal ketamine as an adjuvant for postoperative analgesia after abdominal gynecological surgery using Lidocaine epidural blockade. Anesth Anal. 2000; 91(6): 1479-82.

What is claimed is:

1. A method of treating recurrent thoughts of death, suicidal ideation or suicidal attempts, consisting of intranasally administering to a patient who suffers from at least one of said recurrent thoughts of death, suicidal ideation or suicidal attempts a composition consisting of ketamine at a dosage sufficient to alleviate said recurrent thoughts of death, suicidal ideation or suicidal attempts and at least one pharmaceutically acceptable excipient.

2. The method of claim 1, wherein the recurrent thoughts of death, suicidal ideation or suicidal attempts are alleviated within 2 hours intranasal administration of said ketamine.

3. The method of claim 1, wherein a single intranasal administration of said ketamine is sufficient to alleviate said recurrent thoughts of death, suicidal ideation or suicidal attempts for 7 days.

4. A method of treating recurrent thoughts of death, suicidal ideation or suicidal attempts which consists of intranasally administering to a patient who suffers from at least one of said recurrent thoughts of death, suicidal ideation or suicidal attempts a composition containing a first component consisting of ketamine at a dosage sufficient to alleviate said recurrent thoughts of death, suicidal ideation or suicidal attempts and a second component comprising at least one pharmaceutically acceptable excipient.

5. The method of claim 4 which comprises instranasal administration of multiple doses of said composition.

6. The method of claim 4 which comprises instranasal administration of a single doses of said composition.

7. The method of claim 4 which comprises instranasal administering said ketamine at a doses of between about 0.1 mg/kg per day to about 3.0 mg/kg/day.

8. The method of claim 4, wherein the recurrent thoughts of death, suicidal ideation or suicidal attempts are alleviated within 2 hours intranasal administration of said ketamine.

9. The method of claim 4, wherein a single intranasal administration of said ketamine is sufficient to alleviate said recurrent thoughts of death, suicidal ideation or suicidal attempts for 7 days.

* * * * *

UNITED STATES PATENT AND TRADEMARK OFFICE
CERTIFICATE OF CORRECTION

| | | |
|---|---|---|
| PATENT NO. | : 9,539,220 B2 | Page 1 of 1 |
| APPLICATION NO. | : 14/197767 | |
| DATED | : January 10, 2017 | |
| INVENTOR(S) | : Dennis S. Charney et al. | |

It is certified that error appears in the above-identified patent and that said Letters Patent is hereby corrected as shown below:

In the Specification

Column 1, Lines 9-13 should read:
--GOVERNMENT CLAUSE
This invention was made with government support under MH002587 awarded by The National Institutes of Health. The government has certain rights in the invention.--

Signed and Sealed this
Tenth Day of October, 2017

Joseph Matal
*Performing the Functions and Duties of the*
*Under Secretary of Commerce for Intellectual Property and*
*Director of the United States Patent and Trademark Office*